(12) United States Patent
Frazier et al.

(10) Patent No.: US 7,997,266 B2
(45) Date of Patent: Aug. 16, 2011

(54) SYSTEM AND METHOD FOR AIRWAY MANIPULATION

(75) Inventors: Andrew Frazier, Sunnyvale, CA (US); Chad C. Roue, San Jose, CA (US); Michael T. Dineen, Portola Valley, CA (US); Erik J. van der Burg, Los Gatos, CA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 1646 days.

(21) Appl. No.: 10/958,205

(22) Filed: Oct. 4, 2004

(65) Prior Publication Data
US 2006/0070626 A1   Apr. 6, 2006

(51) Int. Cl.
*A61M 15/00* (2006.01)
*A61M 16/00* (2006.01)
*A61F 2/06* (2006.01)
*A61F 2/02* (2006.01)
*A61F 2/08* (2006.01)
*A61F 2/04* (2006.01)

(52) U.S. Cl. ......... 128/200.24; 128/200.26; 128/207.14; 128/207.15; 128/207.16; 623/1.15; 623/1.18; 623/1.2; 623/1.22; 623/1.36; 623/11.11; 623/14.11; 623/23.64; 623/23.7

(58) Field of Classification Search ............. 128/200.26, 128/207.14, 207.15, 207.16, 200.24; 623/1.15, 623/1.18, 1.2, 1.22, 1.36, 11.11, 14.11, 23.64, 623/23.7
See application file for complete search history.

(56) References Cited

U.S. PATENT DOCUMENTS

| | | | |
|---|---|---|---|
| 4,366,815 A | 1/1983 | Broomes | |
| 4,700,697 A | 10/1987 | Mundell et al. | |
| 4,830,008 A | 5/1989 | Meer | |
| 4,840,172 A * | 6/1989 | Augustine et al. | ....... 128/207.14 |
| 4,978,323 A | 12/1990 | Freedman | |
| 5,123,425 A | 6/1992 | Shannon, Jr. et al. | |
| 5,176,617 A | 1/1993 | Fischell et al. | |
| 5,176,618 A | 1/1993 | Freedman | |
| 5,178,156 A | 1/1993 | Takishima et al. | |
| 5,464,011 A * | 11/1995 | Bridge | ..................... 128/207.14 |
| 6,079,413 A | 6/2000 | Baran | |
| 6,240,316 B1 | 5/2001 | Richmond et al. | |
| 6,668,834 B1 | 12/2003 | Zikria | |
| 6,770,022 B2 | 8/2004 | Mechlenburg et al. | |
| 6,997,189 B2 * | 2/2006 | Biggs et al. | ................... 128/898 |
| 2002/0049479 A1 | 4/2002 | Pitts | |

(Continued)

FOREIGN PATENT DOCUMENTS
JP   2003265621 A   9/2003

OTHER PUBLICATIONS

Malhotra, et al., "Postural Effects on Pharyngeal Protective Reflex Mechanisms," Sleep, vol. 27, No. 6, 2004, pp. 1105-1112.

*Primary Examiner* — Patricia M Bianco
*Assistant Examiner* — Nihir Patel

(57) ABSTRACT

Methods and devices are disclosed for manipulating the airway, such as to treat obstructive sleep apnea. An implant is positioned within the body with respect to the airway. The spatial orientation of the airway is manipulated, directly or indirectly, to affect the configuration of the airway. In general, the implant is manipulated to displace the trachea in an inferior direction, resist superior displacement of the trachea and/or to alter the tracheal wall tension. The implant restrains the trachea in the manipulated configuration.

16 Claims, 32 Drawing Sheets

U.S. PATENT DOCUMENTS

| | | |
|---|---|---|
| 2003/0040790 A1* | 2/2003 | Furst .................... 623/1.11 |
| 2003/0149488 A1 | 8/2003 | Metzger et al. |
| 2004/0049102 A1 | 3/2004 | Nelson et al. |
| 2004/0112390 A1 | 6/2004 | Brooks et al. |
| 2004/0134491 A1* | 7/2004 | Pflueger et al. ......... 128/200.24 |
| 2004/0139975 A1 | 7/2004 | Nelson et al. |
| 2004/0149290 A1 | 8/2004 | Nelson et al. |
| 2004/0172054 A1 | 9/2004 | Metzger et al. |

* cited by examiner

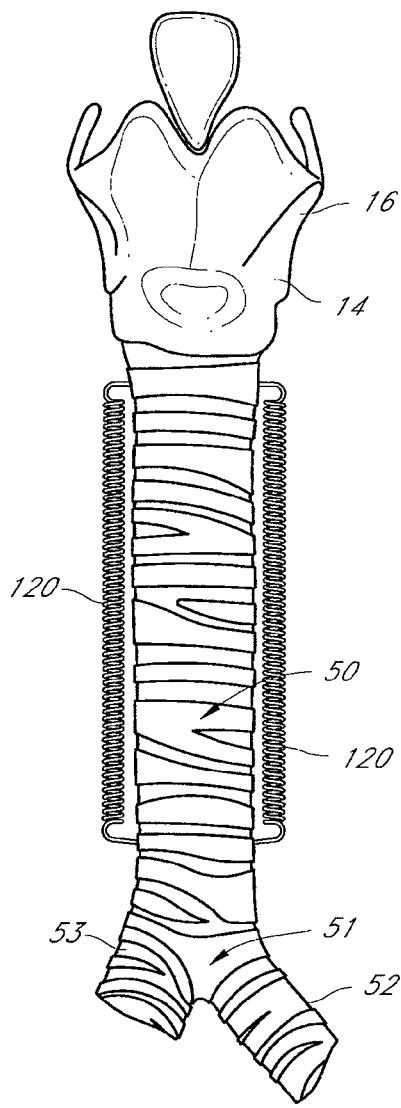
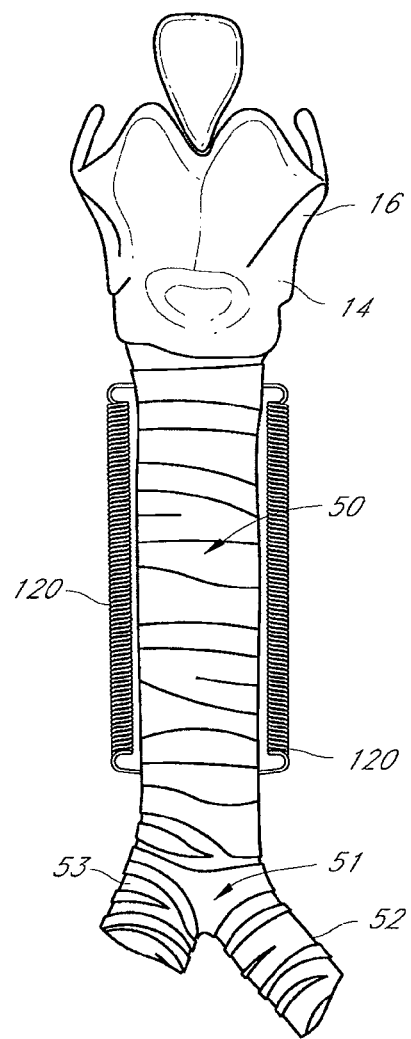
FIG. 12A
FIG. 12B

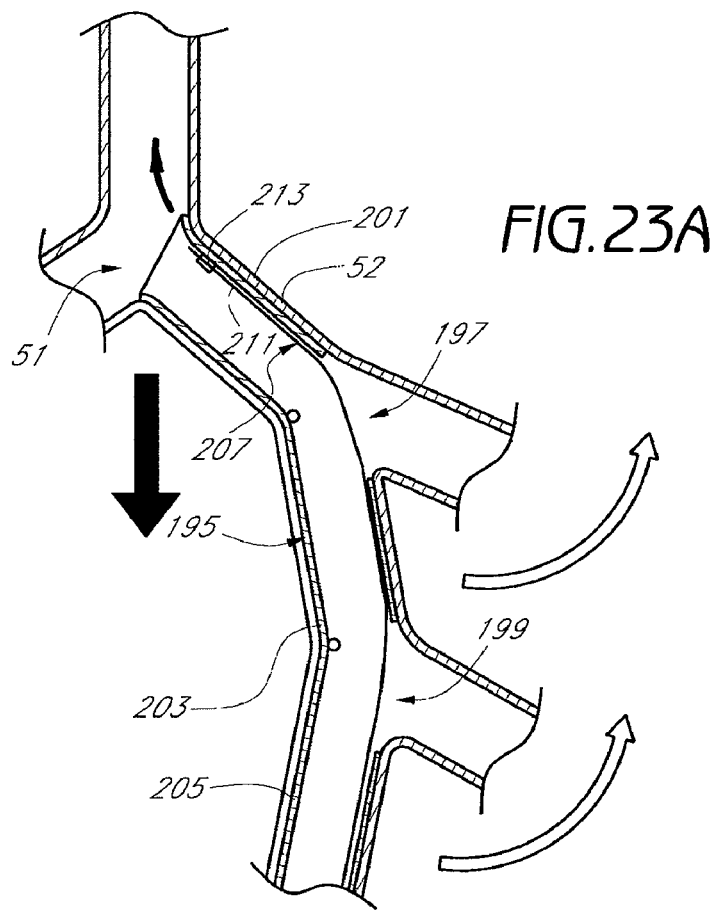
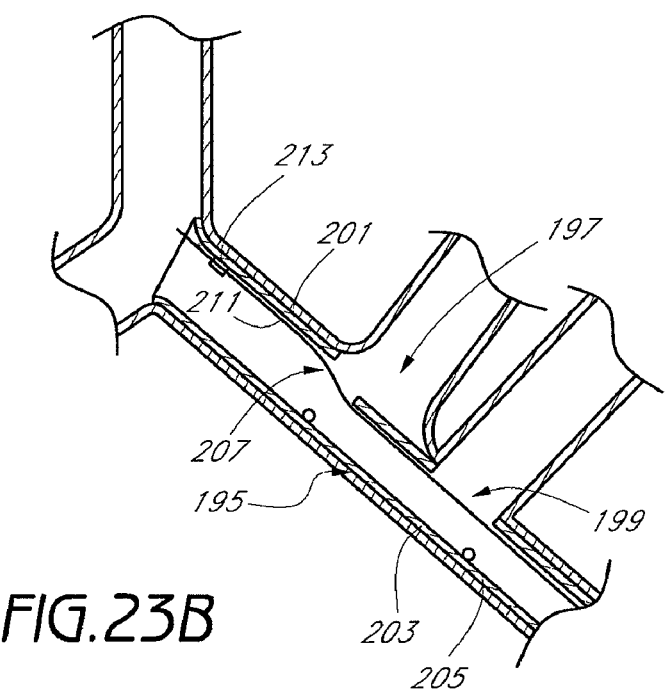

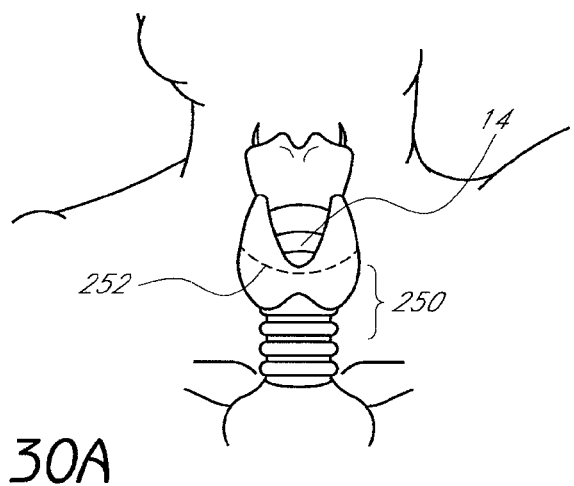
FIG. 30A
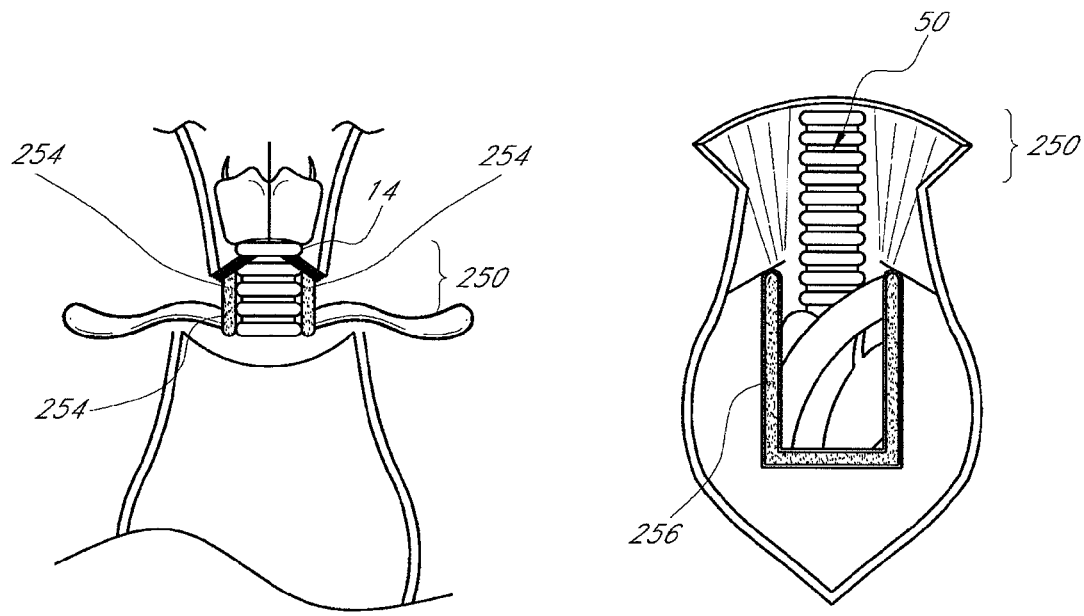
FIG. 30B
FIG. 30C

SYSTEM AND METHOD FOR AIRWAY MANIPULATION

BACKGROUND OF THE INVENTION

1. Field of the Invention

This invention relates generally to a system and method for treating upper airway obstruction, sleep disordered breathing, upper airway resistance syndrome and snoring by manipulating the trachea and/or esophagus.

2. Description of the Related Art

Respiratory disorders during sleep are recognized as a common disorder with significant clinical consequences. During the various stages of sleep, the human body exhibits different patterns of brain and muscle activity. In particular, the REM sleep stage is associated with reduced or irregular ventilatory responses to chemical and mechanical stimuli and a significant degree of muscle inhibition. This muscle inhibition may lead to relaxation of certain muscle groups, including but not limited to muscles that maintain the patency of the upper airways, and create a risk of airway obstruction during sleep. Because muscle relaxation narrows the lumen of the airway, greater inspiratory effort may be required to overcome airway resistance. This increased inspiratory effort paradoxically increases the degree of airway resistance and obstruction through a Bernoulli effect on the flaccid pharyngeal walls during REM sleep.

Obstructive Sleep Apnea (OSA) is a sleep disorder that affects up to 2 to 4% of the population in the United States. OSA is characterized by an intermittent cessation of airflow in the presence of continued inspiratory effort. When these obstructive episodes occur, an affected person will transiently arouse, regain muscle tone and reopen the airway. Because these arousal episodes typically occur 10 to 60 times per night, sleep fragmentation occurs which produces excessive daytime sleepiness. Some patients with OSA experience over 100 transient arousal episodes per hour.

In addition to sleep disruption, OSA may also lead to cardiovascular and pulmonary disease. Apnea episodes of 60 seconds or more have been shown to decrease the partial pressure of oxygen in the lung alveoli by as much as 35 to 50 mm Hg. Some studies suggest that increased catecholamine release in the body due to the low oxygen saturation causes increases in systemic arterial blood pressure, which in turn causes left ventricular hypertrophy and eventually left heart failure. OSA is also associated with pulmonary hypertension, which can result in right heart failure.

Radiographic studies have shown that the site of obstruction in OSA is isolated generally to the supralaryngeal airway, but the particular site of obstruction varies with each person and multiple sites may be involved. A small percentage of patients with OSA have obstructions in the nasopharynx caused by deviated septums or enlarged turbinates. These obstructions may be treated with septoplasty or turbinate reduction procedures, respectively. More commonly, the oropharynx and the hypopharynx are implicated as sites of obstruction in OSA. Some studies have reported that the occlusion begins with the tongue falling back in an anterior-posterior direction (A-P) to contact with the soft palate and posterior pharyngeal wall, followed by further occlusion of the lower pharyngeal airway in the hypopharynx. This etiology is consistent with the physical findings associated with OSA, including a large base of tongue, a large soft palate, shallow palatal arch and a narrow mandibular arch. Other studies, however, have suggested that increased compliance of the lateral walls of the pharynx contributes to airway collapse. In the hypopharynx, radiographic studies have reported that hypopharyngeal collapse is frequently caused by lateral narrowing of the pharyngeal airway, rather than narrowing in the A-P direction.

OSA is generally diagnosed by performing overnight polysomnography in a sleep laboratory. Polysomnography typically includes electroencephalography to measure the stages of sleep, an electro-oculogram to measure rapid eye movements, monitoring of respiratory effort through intercostal electromyography or piezoelectric belts, electrocardiograms to monitor for arrhythmias, measurement of nasal and/or oral airflow and pulse oximetry to measure to measure oxygen saturation of the blood.

Following the diagnosis of OSA, some patients are prescribed weight loss programs as part of their treatment plan, because of the association between obesity and OSA. Weight loss may reduce the frequency of apnea in some patients, but weight loss and other behavioral changes are difficult to achieve and maintain. Therefore, other modalities have also been used in the treatment of OSA, including pharmaceuticals, non-invasive devices and surgery.

Among the pharmaceutical treatments, respiratory stimulants and drugs that reduce REM sleep have been tried in OSA. Progesterone, theophylline and acetozolamide have been used as respiratory stimulants, but each drug is associated with significant side effects and their efficacy in OSA is not well studied. Protriptyline, a tricyclic antidepressant that reduces the amount of REM sleep, has been shown to decrease the frequency of apnea episodes in severe OSA, but is associated with anti-cholinergic side effects such as impotence, dry mouth, urinary retention and constipation.

Other modalities are directed at maintaining airway patency during sleep. Oral appliances aimed at changing the position of the soft palate, jaw or tongue are available, but patient discomfort and low compliance have limited their use. Continuous Positive Airway Pressure (CPAP) devices are often used as first-line treatments for OSA. These devices use a sealed mask which produce airflow at pressures of 5 to 15 cm of water and act to maintain positive air pressure within the pharyngeal airway and thereby maintain airway patency. Although CPAP is effective in treating OSA, patient compliance with these devices is low for several reasons. Sleeping with a sealed nasal mask is uncomfortable for patients. Smaller sealed nasal masks may be more comfortable to patients but are ineffective in patients who sleep with their mouths open, as the air pressure will enter the nasopharynx and then exit the oropharynx. CPAP also causes dry nasal passages and congestion.

Surgical treatments for OSA avoid issues with patient compliance and are useful for patients who fail conservative treatment. One surgery used for OSA is uvulopalatopharyngoplasty (UPPP). UPPP attempts to improve airway patency in the oropharynx by eliminating the structures that contact the tongue during sleep. This surgery involves removal of the uvula and a portion of the soft palate, along with the tonsils and portions of the tonsillar pillars. Although snoring is reduced in a majority of patients who undergo UPPP, the percentage of patients who experience reduced frequency of apnea episodes or improved oxygen saturation is substantially lower. Postoperatively, many patients that have undergone UPPP continue to exhibit oropharyngeal obstruction or concomitant hypopharyngeal obstruction. Nonresponders often have physical findings of a large base of tongue, an omega-shaped epiglottis and redundant aryepiglottic folds. UPPP is not a treatment directed at these structures. UPPP also exposes patients to the risks of general anesthesia and postoperative swelling of the airway that will require a tracheostomy. Excessive tissue removal may also cause regurgitation of food and liquids into the nasopharynx.

Laser-assisted uvulopalatopharyngoplasty (LAUP) is a similar procedure to UPPP that uses a CO2 laser to remove the uvula and portions of the soft palate, but the tonsils and the lateral pharyngeal walls are not removed.

For patients who fail UPPP or LAUP, other surgical treatments are available but these surgeries entail significantly higher risks of morbidity and mortality. In genioglossal advancement with hyoid myotomy (GAHM), an antero-inferior portion of the mandible, which includes the attachment point of the tongue musculature, is repositioned forward and in theory will pull the tongue forward and increase airway diameter. The muscles attached to the inferior hyoid bone are severed to allow the hyoid bone to move superiorly and anteriorly. Repositioning of the hyoid bone expands the retrolingual airspace by advancing the epiglottis and tongue base anteriorly. The hyoid bone is held in its new position by attaching to the mandible using fascia. Variants of this procedure attach the hyoid bone inferiorly to the thyroid cartilage.

A laser midline glossectomy (LMG) has also been tried in some patients who have failed UPPP and who exhibit hypopharyngeal collapse on radiographic studies. In this surgery, a laser is used to resect the midline portion of the base of the tongue. This involves significant morbidity and has shown only limited effectiveness.

In some patients with craniofacial abnormalities that include a receding mandible, mandibular or maxillomandibular advancement surgeries may be indicated for treatment of OSA. These patients are predisposed to OSA because the posterior mandible position produces posterior tongue displacement that causes airway obstruction. In a mandibular advancement procedure, the mandible is cut bilaterally posterior to the last molar and advanced forward approximately 10 to 14 mm. Bone grafts are used to bridge the bone gap and the newly positioned mandible is wire fixated to the maxilla until healing occurs. Mandibular advancement may be combined with a Le Fort I maxillary osteotomy procedure to correct associated dental or facial abnormalities. These procedures have a high morbidity and are indicated only in refractory cases of OSA.

Experimental procedures described in the clinical literature for OSA include the volumetric radiofrequency tissue ablation and hyoidplasty, where the hyoid bone is cut into several segments and attached to a brace that widens the angle of the U-shaped hyoid bone. The latter procedure has been used in dogs to increase the pharyngeal airway lumen at the level of the hyoid bone. The canine hyoid bone, however, is unlike a human hyoid bone because the canine hyoid bone comprises nine separate and jointed bones, while the human hyoid bone comprises five bones that are typically fused together.

Notwithstanding the foregoing, there remains a need for improved methods and devices for treating obstructive sleep apnea.

SUMMARY OF THE INVENTION

There is provided in accordance with one aspect of the present invention, a method of treating apnea. The method comprises the steps of securing a device with respect to a trachea, the trachea having a superior direction and an inferior direction. The device is manipulated to advance at least a portion of the trachea in the inferior direction. The securing step may comprise securing the device to the trachea. The securing step may also comprise securing the device to tissue adjacent the trachea, such as the hypopharynx, esophagus and/or bronchi. The device may initially be positioned within the trachea, or adjacent the trachea. The manipulating step may comprise placing the device under tension to pull or push at least a portion of the trachea in an inferior direction. The manipulating step may comprise radially expanding the device within the trachea. The manipulating step may alternatively comprise adjusting the device to change the angle between first and second bronchial tubes.

In accordance with another aspect of the present invention, there is provided a method of treating a patient. The method comprises the steps of providing a tracheal device having a first end with a first attachment structure, and a second end with a second attachment structure. The first attachment structure is attached to a first point on or within the trachea, and the second attachment structure is attached to a second point on or within the trachea. The distance between the first and second attachment points is thereafter shortened.

In accordance with a further aspect of the present invention, there is provided a tracheoesophageal implant. The implant comprises an elongate body, adapted for positioning on or within the esophagus. A first attachment structure is provided on the body, and a second attachment structure is provided on the body, spaced apart from the first attachment structure. The implant is configured for positioning on or within the esophagus and for attaching to the esophageal wall. The implant is further adapted to manipulate the spacing between the first attachment structure and second attachment to indirectly affect the portion of the trachea around and between the first and second attachment points.

In accordance with a further aspect of the present invention, there is provided a tracheal implant. The implant comprises an elongate body, adapted for positioning on or within the trachea. A first attachment structure is provided on the body, and a second attachment structure is provided on the body, spaced apart from the first attachment structure. The implant is configured for positioning on or within the trachea and for attaching to the tracheal wall. The implant is further adapted to manipulate the spacing between the first attachment structure and second attachment structure to affect the portion of the trachea about the region between the first and second attachment points. The implant is adaptable for placement in the esophagus or tissue adjacent to the trachea, thereby affecting the trachea indirectly. Adjacent tissue to the trachea includes but is not limited to the esophagus, clavicles, ribs, bronchi and carina.

In accordance with another aspect of the present invention, there is provided a method of treating a patient. The method comprises the steps of providing an airway manipulation device having a first end with a first attachment structure, and a second end with a second attachment structure. The first attachment structure is attached to a first point on or within the airway, and the second attachment structure is attached to a second point on or within the airway. The distance between the first and second attachment points is thereafter altered.

In accordance with a further aspect of the present invention, there is provided a tracheal remodeling device. The remodeling device comprises a main body portion, for positioning on or within the trachea. A first branch portion is provided, for positioning on or within a first bronchial tube. A second branch portion is provided, for positioning on or within a second bronchial tube. The angle between the first and second bronchial tube portions is adjustable throughout a range from a first angle, which approximates the normal anatomical relationship, to a second angle, which places inferior direction tension on the trachea. The remodeling device is configured to retain the second angle. The angle between the first bronchial tube and trachea may also be adjustable separately from the angle between the second bronchial tube and the trachea. The angle between the second bronchial tube and trachea may also be adjustable separately from the angle between the first bronchial tube and the trachea. The angle between the second bronchial tube and the trachea may also be fixed.

In one embodiment of the invention, an airway remodeling device is provided. The device comprises a first segment for positioning within a first portion of the airway, and a second segment for positioning within a second portion of the airway, wherein the angle between the first portion of the airway and second portion of the airway is adjustable throughout a range from a first angle to a second angle, and configured to retain the second angle. The device may also comprise a third segment for positioning within a third portion of the airway, wherein the angle between the third portion of the airway and the adjacent portion of the airway is adjustable through a range from a third angle to a fourth angle, and configured to retain the fourth angle. The adjacent portion of the airway may be the first portion or second portion of the airway. The first segment, second segment and third segment may generally have a Y-configuration or a serial configuration.

Further features and advantages of the present invention will become apparent to those of skill in the art in view of the disclosure herein, when considered together with the attached drawings and claims.

BRIEF DESCRIPTION OF THE DRAWINGS

The structure and method of using the invention will be better understood with the following detailed description of embodiments of the invention, along with the accompanying illustrations, in which:

FIGS. 12A and 12B show one embodiment of the invention comprising tracheal shortening implants placed on the exterior surface of the trachea.

FIG. 21B is a cross sectional view of the remodeling stent of FIG. 21A.

FIG. 21C is a schematic elevational view of the stent of FIG. 21A following fixation of the stent.

FIGS. 23A and 23B are cross sectional views of the fixation of one embodiment of a unilateral remodeling stent

FIGS. 30A through 30C illustrate one embodiment for surgically accessing the trachea.

DETAILED DESCRIPTION OF THE PREFERRED EMBODIMENT

The present invention provides methods and devices for manipulating the airway. It is hypothesized that the laxity in pharyngeal structures contributes to the pathophysiology of obstructive sleep apnea, snoring, upper airway resistance and sleep disordered breathing. This laxity may be intrinsic to the pharyngeal structures and/or may be affected by interrelationships between pharyngeal structures and other body structures. For example, in the upright position, gravity lessens the effect of abdominal cavity organs on the diaphragm. When in the prone or supine position, however, the contents of the abdominal cavity have a greater tendency to displace the diaphragm superiorly, which in turn displaces the lungs, bronchi and trachea and other portions of the airway superiorly and accentuates the laxity of the pharyngeal structures by reducing the tissue tension normally applied by the airway on the laryngeal structures. The embodiments of the invention, however, are not restricted or limited to these mechanisms or hypotheses.

In some embodiments of the invention, airway manipulation is performed by displacing at least a portion of the airway inferiorly relative to other body structures. In some embodiments of the invention, airway manipulation may also comprise increasing the wall tension of the airway without necessarily displacing the airway. In some embodiments, airway manipulation comprises resisting superior displacement of the airway that occurs either continuously or intermittently with sleep related disorders or other respiratory problems. In some embodiments, airway manipulation comprises applying a force with an inferior directional component to at least a portion of the airway. Airway manipulation can be performed directly on the airway, or indirectly through tissues or structures adjacent to the airway.

Figure 1:
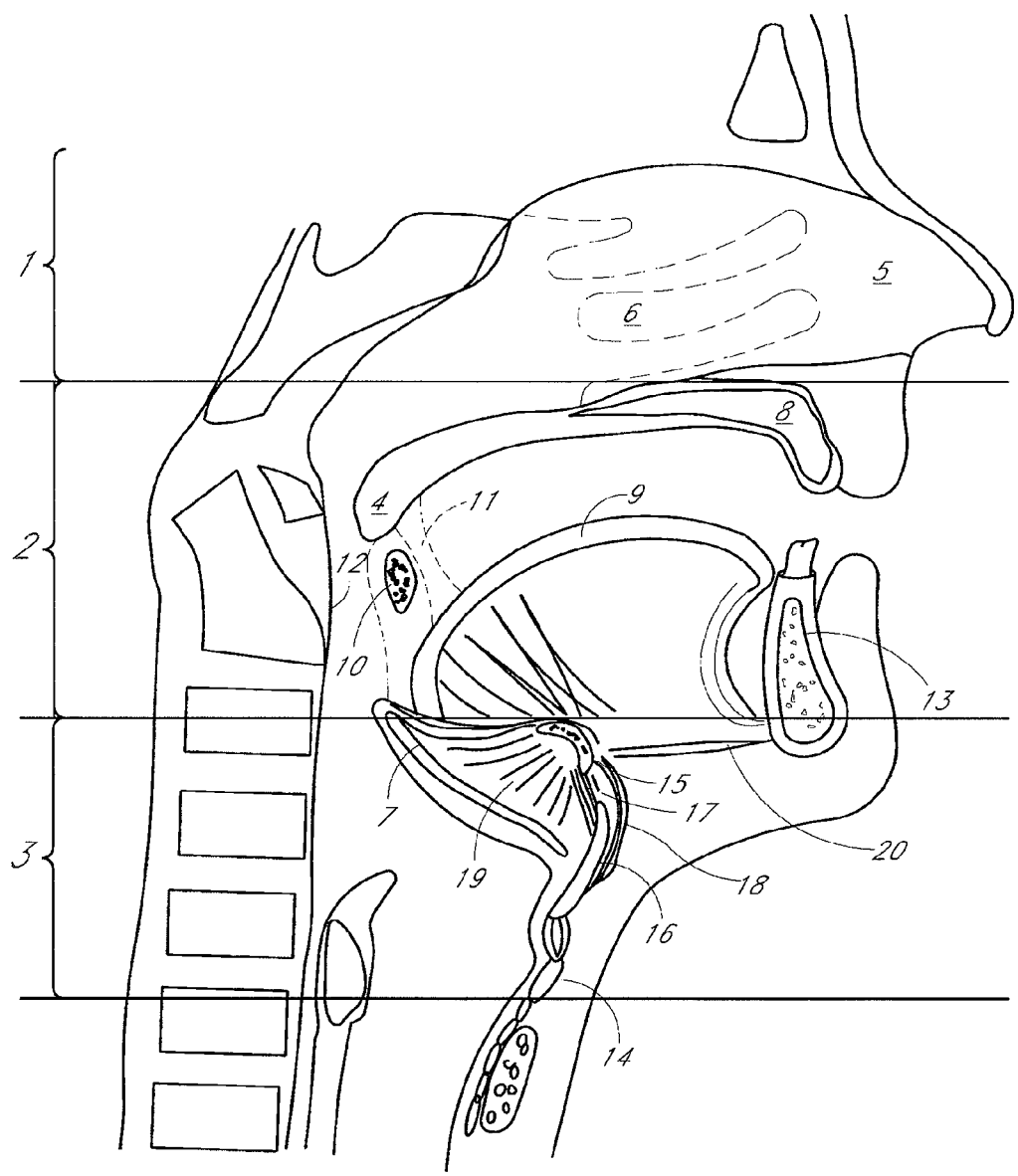
FIG. 1 is a sagittal view of the pharynx.

FIG. 1 is a sagittal view of the structures that comprise the pharyngeal airway and may be involved in obstructive sleep apnea. The pharynx is divided, from superior to inferior, into the nasopharynx 1, the oropharynx 2 and the hypopharynx 3. The nasopharynx 1 is a less common source of obstruction in OSA. The nasopharynx is the portion of the pharynx above the soft palate 4. In the nasopharynx, a deviated nasal septum 5 or enlarged nasal turbinates 6 may occasionally contribute to upper airway resistance or blockage. Only rarely, a nasal mass, such as a polyp, cyst or tumor may be a source of obstruction.

The oropharynx 2 comprises structures from the soft palate 4 to the upper border of the epiglottis 7 and includes the hard palate 8, tongue 9, tonsils 10, palatoglossal arch 11, the posterior pharyngeal wall 12 and the mandible 13. An obstruction in the oropharynx 2 may result when the tongue 9 is displaced posteriorly during sleep as a consequence of reduced muscle activity during REM sleep. The displaced tongue 9 may push the soft palate 4 posteriorly and may seal off the nasopharynx 1 from the oropharynx 2. The tongue 9 may also contact the posterior pharyngeal wall 12, which causes further airway obstruction.

The hypopharynx 3 comprises the region from the upper border of the epiglottis 7 to the inferior border of the cricoid cartilage 14. The hypopharynx 3 further comprises the hyoid bone 15, a U-shaped, free floating bone that does not articulate with any other bone. The hyoid bone 15 is attached to surrounding structures by various muscles and connective tissues. The hyoid bone 15 lies inferior to the tongue 9 and superior to the thyroid cartilage 16. A thyrohyoid membrane 17 and a thyrohyoid muscle 18 attaches to the inferior border of the hyoid 15 and the superior border of the thyroid cartilage 16. The epiglottis 7 is infero-posterior to the hyoid bone 15 and attaches to the hyoid bone by a median hyoepiglottic ligament 19. The hyoid bone attaches anteriorly to the infero-posterior aspect of the mandible 13 by the geniohyoid muscle 20.

Figure 2C:
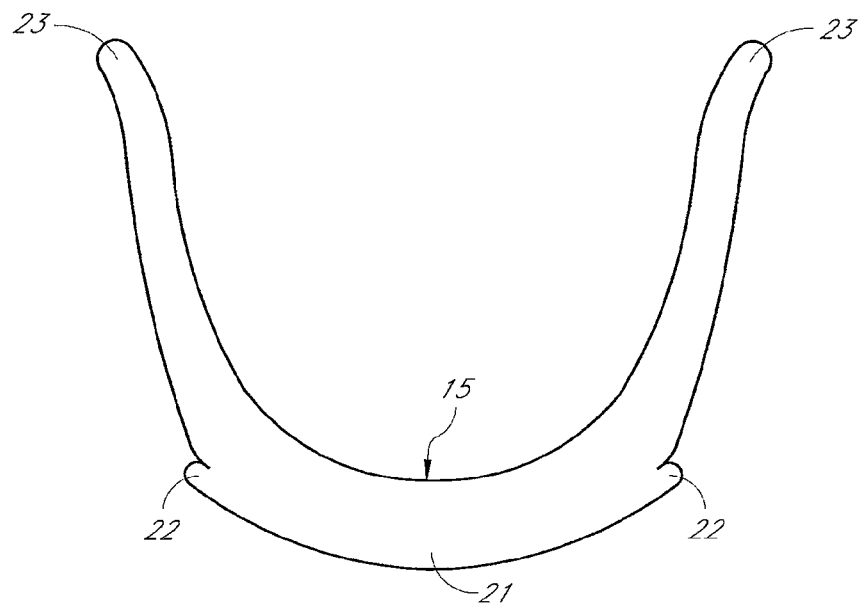
FIG. 2C is a superior view of the hyoid bone.
Figures 2A, 2B:
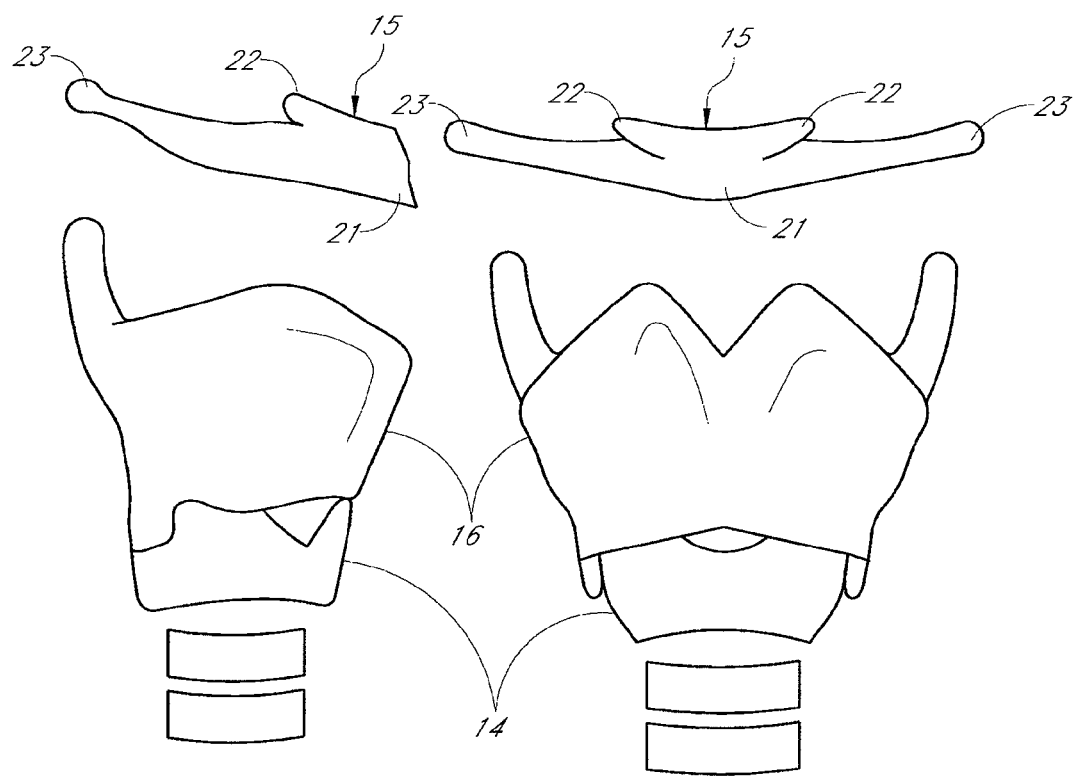
FIGS. 2A and 2B depict the hyoid bone with respect to the thyroid and cricoid cartilage in a lateral and anterior view, respectively.
Figure 3:
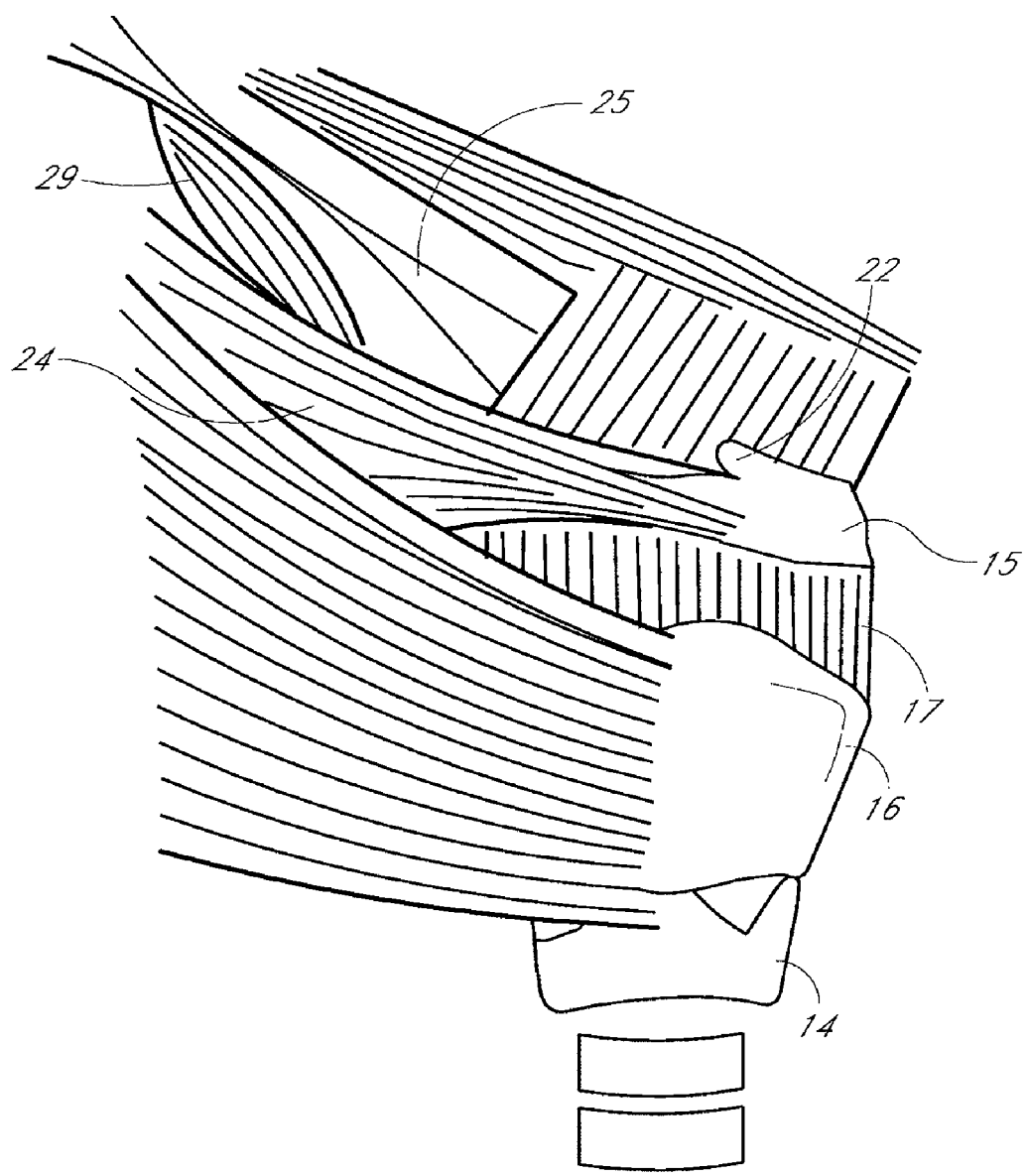
FIG. 3 illustrates the musculature attached to the hyoid bone in a lateral view.
Figure 4:
FIG. 4 shows an anterior view of the musculature attached to the hyoid bone. The anatomical right portion of the body depicts the deep musculature and the anatomical left portion of the body shows the superficial musculature.

The position of the hyoid bone relative to the thyroid and cricoid cartilage is shown in FIGS. 2A and 2B. The hyoid bone is a U-shaped bone comprising a body 21, two lesser horns 22 and two greater horns 23, as a shown in a superior view in FIG. 2C. As shown in FIG. 3, at the pharyngeal level of the hyoid bone, the hyoid bone forms an anterior portion of the pharynx while a pair of middle pharyngeal constrictor muscles 24 forms the remaining portions of the airway. The muscle fibers of the middle constrictor muscles 24 originate from the greater 23 and lesser horns 22 of the hyoid bone 15 and fan out posteriorly, inferiorly and superiorly to the posterior midline pharynx (not shown). A stylohyoid ligament 25 attaches from the cranium to the hyoid bone. FIG. 4 illustrates the attachments of the extrinsic muscles of the larynx. The left side of the illustration in FIG. 4 depicts the anatomy of the superficial musculature and the right side depicts the deeper musculature. The posterior belly 26 of the digastric muscle originates from the mastoid process 27 and attaches to the lesser horn 22 of the hyoid bone 15 as a tendon and then attaches as an anterior belly 28 to the mandible 13. The stylohyoid muscle 29 originates from the styloid process (not shown) of the cranium and then splits into two portions upon inserting adjacent to the lesser horn of the hyoid bone 15 to allow the digastric muscle to pass anteriorly. Deep to the digastric 26, 28 and stylohyoid 29 muscles are the hyoglossus muscles 30, attaching to the superior surfaces of the greater horns 23 of the hyoid bone 15 and inserting into the lateral areas of the tongue 9. Further deep is the mylohyoid muscle 31, a sheet of muscle that courses between the hyoid bone 15 and the lateral interior sides of the mandible 13, forming a portion of the musculature of the floor of the mouth along with the geniohyoid muscle 20. These muscles move the hyoid bone 15 and tongue 9 superiorly and anteriorly, and are involved in the act of swallowing. Overlying most of the antero-lateral neck is the platysma muscle (not shown) that originates over the upper anterior chest and inserts over the anterior surfaces of the mandible 13.

The omohyoid muscles are the most lateral of the muscles that attach to the inferior surface of the hyoid bone 15. The omohyoid muscles have two bellies 33, 34. The inferior belly 33 attaches to the scapula and the superior belly 34 attaches to the inferior body of the hyoid bone. The two bellies 33, 34 are joined by a tendon 32 that is continuous with fascia along the medial ends of the clavicles 46. Also attached to the inferior surfaces of the hyoid bone 15 are the sternohyoid muscles 35 that originate at the manubrium 36 of the sternum and the thyrohyoid 18 muscles that originate along antero-inferior border of the thyroid cartilage 16. The inferior muscles of the hyoid bone act to increase the luminal opening of the pharynx at the level of the hyoid.

Figure 5:
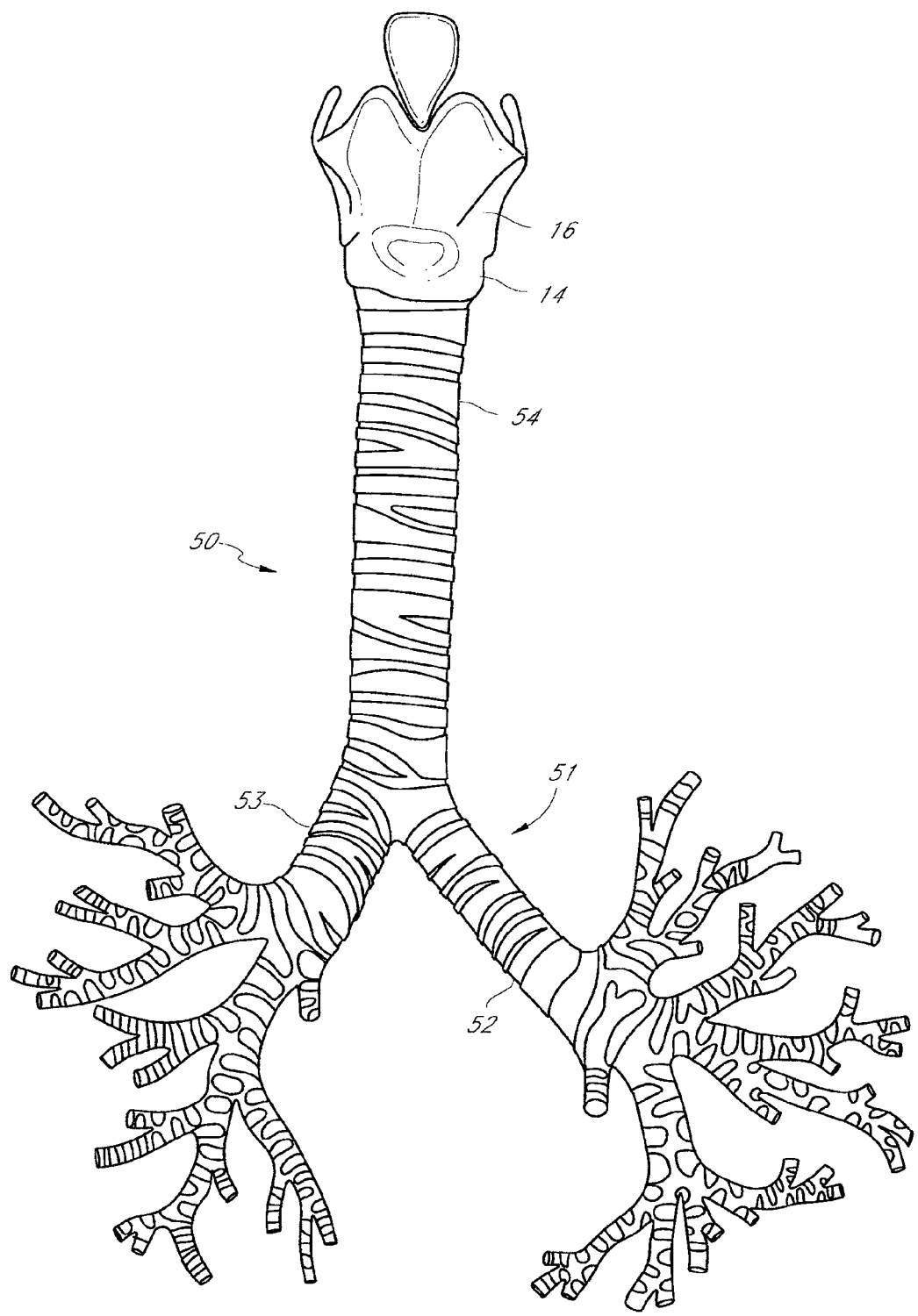
FIG. 5 shows an anterior view of the trachea relative to the laryngeal structures and the bronchial tree.

FIG. 5 depicts a trachea relative to the laryngeal structures and the bronchial tree. The trachea 50 courses from a subcutaneous position in the neck to a position against the esophagus and prevertebral fascia at the level of the carina 51. The carina 51 bifurcates into the left and right mainstem bronchi 52, 53 at the level of the fifth thoracic vertebral body and can be localized approximately at the same level as the sternal notch. The average length of the adult trachea is about 11 cm from the inferior border of the cricoid cartilage to the carina 51. The trachea 51 may range from about 9 cm to about 15 cm. The trachea 51 has an average internal diameter of about 2.3 cm laterally and about 1.8 cm anteroposteriorly. The left mainstem bronchus 52 has an average length of about 4.5 cm and leaves the trachea at about a 135 degree angle. The right mainstem bronchus 53 measures on average about 2.5 cm in length, is located slightly superior compared to the left mainstem bronchus 52 and branches from the carina 51 at about a 155 degree angle.

There are typically about 18 to about 22 horseshoe-shaped cartilaginous rings 54 in the human trachea, with approximately two rings per centimeter. Each ring is about 4 mm in height and is separated from adjacent rings by about 2 mm of connective tissue. The horseshoe-shaped rings give the posterior wall of the trachea 50 a slightly flattened appearance. This posterior wall is also known as the membranous trachea. The airway in an adult is roughly elliptical. The only complete cartilaginous ring in the normal airway is the cricoid cartilage 14 of the larynx.

Calcification of the cricoid cartilage 14 is not unusual, and calcification of other cartilaginous rings occurs with age. The trachea 50 is not rigidly fixed to the surrounding tissue and provides relatively free vertical movement in relation to other anatomic structures. The most rigid point of fixation below the cricoid cartilage 14 lies where the aortic arch forms a sling over the left mainstem bronchus 52. By transecting the suprahyoid musculature, the inferior mobility of the trachea 50 may be further increased.

In the region of the neck, the anterior surface of the trachea 51 is covered from a superior to inferior direction, by the isthmus of the thyroid gland, the inferior thyroid veins, the sternothyroid and sternohyoid muscles, the cervical fascia and by the branches of the anterior jugular veins. Laterally, the trachea is adjacent to the common carotid arteries, the right and left lobes of the thyroid gland, the inferior thyroid arteries and the recurrent laryngeal nerves.

In the thoracic cavity, the trachea is covered anteriorly by the manubrium and sternum, the remains of the thymus gland, the inominate vein, the aortic arch, the inominate and left common carotid arteries and the deep cardiac plexus. Posteriorly, the trachea is in contact with the esophagus, which lies in contact with the membranous trachea, typically just to the left from the midline of the trachea. The esophagus is a hollow muscular tube approximately 18 cm to 26 cm in length that begins superiorly where the inferior constrictor muscle merges with the cricopharyngeus muscle to form the upper esophageal sphincter. The esophagus maintains a radially collapsed configuration except during swallowing, where the esophageal lumen is capable of expanding up to 2 cm in the AP direction and 3 cm laterally. To the right of the trachea are the right pleural membrane and the right vagus nerve. To the left is the left recurrent laryngeal nerve, the aortic arch, the left common carotid and subclavian arteries. The recurrent laryngeal nerves course along the tracheoesophageal groove on both the right and left sides. The blood supply to the trachea enters the trachea laterally and originates segmentally from the inferior thyroid, internal thoracic, supreme intercostals and the bronchial arteries.

One embodiment of the invention thus provides methods and devices for either reducing the axial length of the trachea, resisting superior direction movement of the trachea, or imparting inferior direction traction on at least a portion of the trachea. In an embodiment adapted for shortening the effective length of the trachea, shortening may occur within the range of from about 5% to about 30%, and, in certain embodiments, between about 10% and 25% of the overall length of the trachea. Shortening can occur by collapsing the connective tissue membranes between adjacent tracheal rings, thereby reducing the spacing between the tracheal rings and reducing the tracheal length. The exact degree of tracheal shortening or inferior direction tracheal traction can be optimized for a given patient, taking into account the desired clinical results.

The foregoing may be accomplished by positioning an implant within the trachea, positioning an implant adjacent but outside of the trachea, or both. In an embodiment extending outside of the trachea, the device may be attached to adjacent tissue structure such as adjacent musculature or bone such as the clavicle bone. An implant placed on or within the esophagus can also be used to indirectly affect the trachea.

Tracheal shortening may also be accomplished by removing or effectively removing tissue from the tracheal wall, followed by an anastomosis of healthy margins of tracheal tissue, which may be adjacent an area of treated tissue. Shortening of the trachea can be accomplished by the shrinking or removal of a segment of the trachea. Tissue removal can be accomplished using any of a variety of endotracheal cutting devices, followed by anastomosis using conventional techniques. Tissue shrinkage and/or removal can be accomplished using any of a variety of energy sources, such as thermal ablation (laser, RF ablation, microwave, ultrasound and the like), cryotherapy, or other techniques known in the art.

Figure 6A:
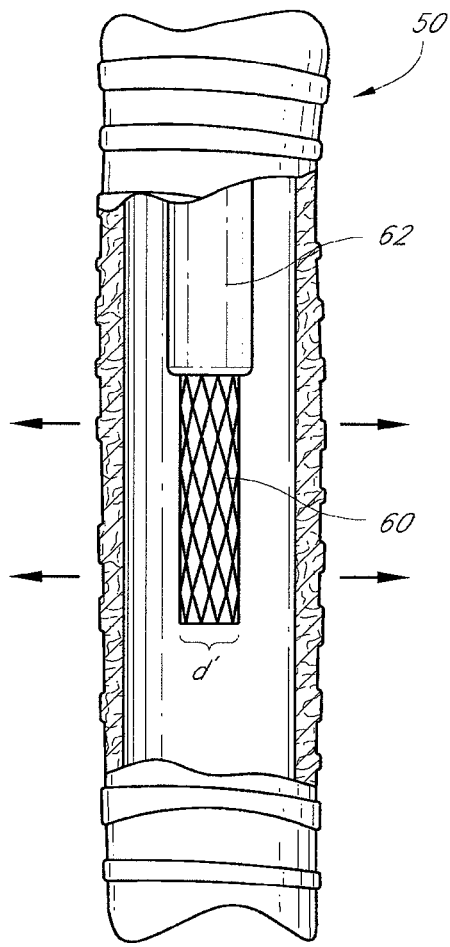
FIGS. 6A and 6B show one embodiment of the invention comprising a radially expandable endotracheal stent for manipulating the trachea.
Figure 6B:
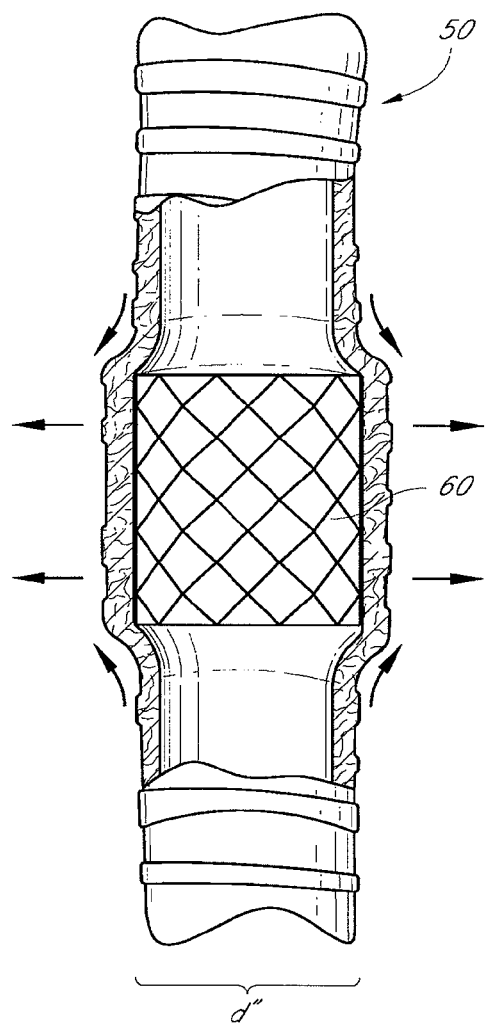

In one embodiment of the invention, a device for remodeling the trachea is provided. FIGS. 6A and 6B show a device comprising an endoscopically deliverable endotracheal stent 60 having a first reduced diameter d' and a second expanded diameter d". In its first reduced diameter d', the stent 60 is capable of mounting in or on a catheter, laryngoscope or bronchoscope 62 for passage through the oropharynx and larynx to the trachea 50. In its second expanded diameter d", the stent 60 is capable of enlarging the diameter of the trachea 50. By taking advantage of Poisson's Ratio, which is the ratio of transverse strain to longitudinal strain of a structure, enlargement of the tracheal diameter may be used to alter the longitudinal characteristics of the trachea 51. In one embodiment, the stent in the second expanded diameter d" causes shortening of the tracheal length, as shown in FIG. 6B. This will cause an inferior displacement of the portion of the trachea 50 superior to the implantation site of the stent 60. By inferiorly moving a portion of the trachea, remodeling of the laryngeal structures superior to the trachea occurs and can alleviate at least a portion of the airway obstruction that occurs in obstructive sleep apnea. In one embodiment, placement of the stent 60 causes increased longitudinal tension in the trachea 50 to remodel the laryngeal structures.

The stent 60 may be expandable in response to an extrinsic force for expansion, such as a balloon. Balloon expandable stent configurations may have a lattice, slotted, helical or any of a variety of configurations as is known in the art. Alternatively, the stent 60 may be a self expandable structure which is restrained in a first, small cross sectional configuration d' for endotracheal navigation, and enlargeable upon removal of a restraint to assume a second, enlarged cross sectional configuration d". Self expandable stents can be constructed to have any of a variety of expansion ratios and radial strength, as is well understood in the cardiovascular arts. For example, endotracheal stents may be constructed from a zig zag wire wall pattern in which the stent comprises a plurality of adjacent segments. Each segment includes a plurality of proximal apexes and a corresponding plurality of distal apexes, connected by walls struts.

The stent may further comprise an anti-migration component for resisting movement of the stent during implantation or with long-term use. The anti-migration component may comprise at least one hook, barb, spike, suture, adhesive or tissue ingrowth surface to further engage the tracheal wall.

In another embodiment of the invention, a device for manipulating the trachea is provided. The device comprises a longitudinal member with at least one proximal end and at least one distal end, wherein the proximal ends and distal ends of the member are adapted to engage a body structure with respect to the trachea. The device may be adapted for endolumenal placement. Endolumenal placement includes but is not limited to the trachea, the airway and/or the esophagus. In one embodiment, at least one end of the longitudinal member is adapted for engaging a portion of the inner tracheal or bronchial wall. The proximal and distal ends may be configured with at least one hook, spike, barb, clip or other configuration known in the art to facilitate engagement of the body structure. In some embodiments, the attachment surface of the body structure may be prepared with drilling, roughening or other treatment to facilitate attachment of the device. The proximal and distal ends may be further configured to engage the respiratory tract between the tracheal or bronchial rings and utilize the integrity of the rings to further secure the device. The proximal ends and distal ends need not have the same configuration.

In one embodiment, the longitudinal member is capable of at least moving the proximal and distal ends closer together along the longitudinal axis of the member. The member may be configured to have internal bias for moving the proximal and distal ends towards each other. The longitudinal member may be capable of elastic deformation in at least the longitudinal direction. In another embodiment, the internal bias may be manually adjustable. The member may be configured to allow manual adjustment of the distance between the ends, without an independent biasing force. In one embodiment, the longitudinal member is capable of moving the proximal and distal ends both closer and farther apart.

Figure 7A:
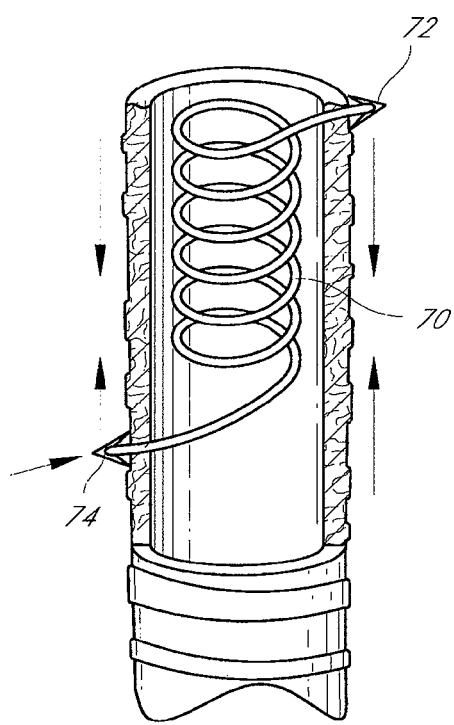
FIGS. 7A and 7B show one embodiment of the invention comprising a longitudinal member with a helical spring structure capable of axially or longitudinally compressing a portion of the trachea.
Figure 7B:
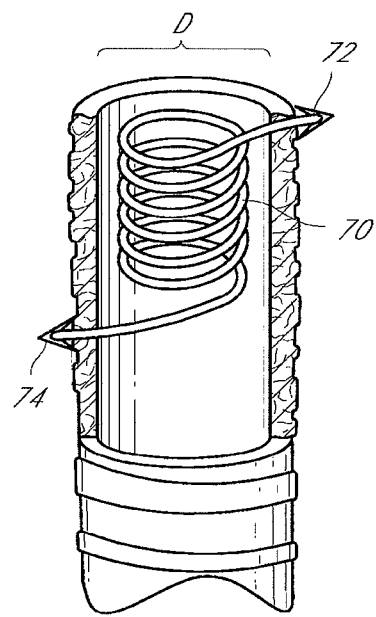
Figure 8A:
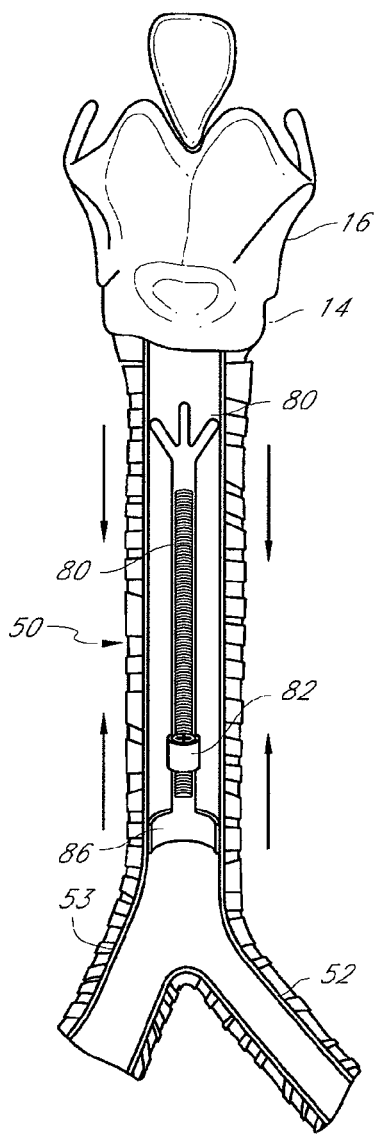
FIGS. 8A and 8B show one embodiment of the invention adapted to attach endolumenally and comprises a slotted tongue with a screw mechanism for altering the distance between the proximal and distal ends of the implant.
Figure 8B:
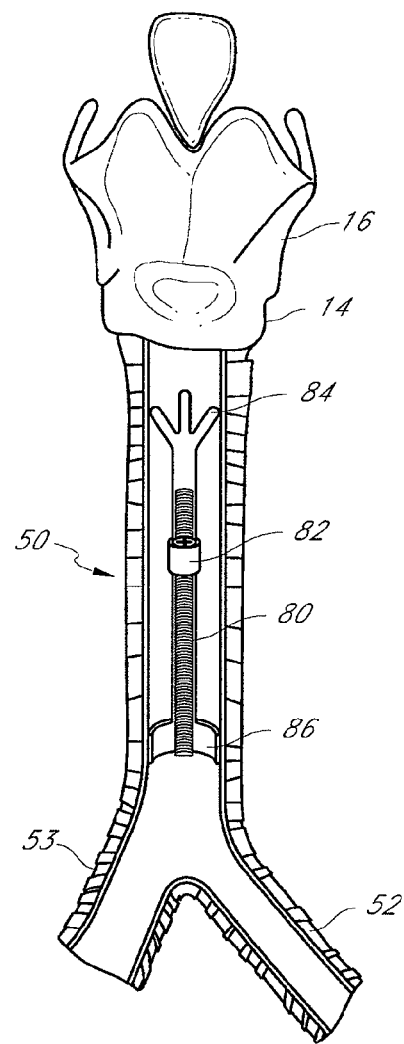

In one embodiment, the longitudinal member comprises an elongate member wherein the proximal and distal ends of the body are each capable of engaging at least one point of the respiratory tract. Multiple devices may be used to achieve the desired tracheal manipulation. In one embodiment of the invention, shown in FIGS. 7A and 7B, the elongate member comprises a helical spring structure 70 having an internal bias capable of moving the two ends closer together. The diameter D of the helical spring structure 70 may range from about 1 mm to about 30 mm. In another embodiment, the diameter ranges from about 3 mm to about 20 mm. In some embodiments of the invention, the device may be capable of both longitudinal shortening between the ends and radial expansion as shown in FIGS. 6A and 6B. In another embodiment, depicted in FIGS. 8A and 8B, the elongate member comprises a slotted structure 80 with adjustable screw 82 capable of altering the distance between the two ends 84, 86 with the application of a rotational force to the screw 82.

Figures 9A, 9B, 9C:
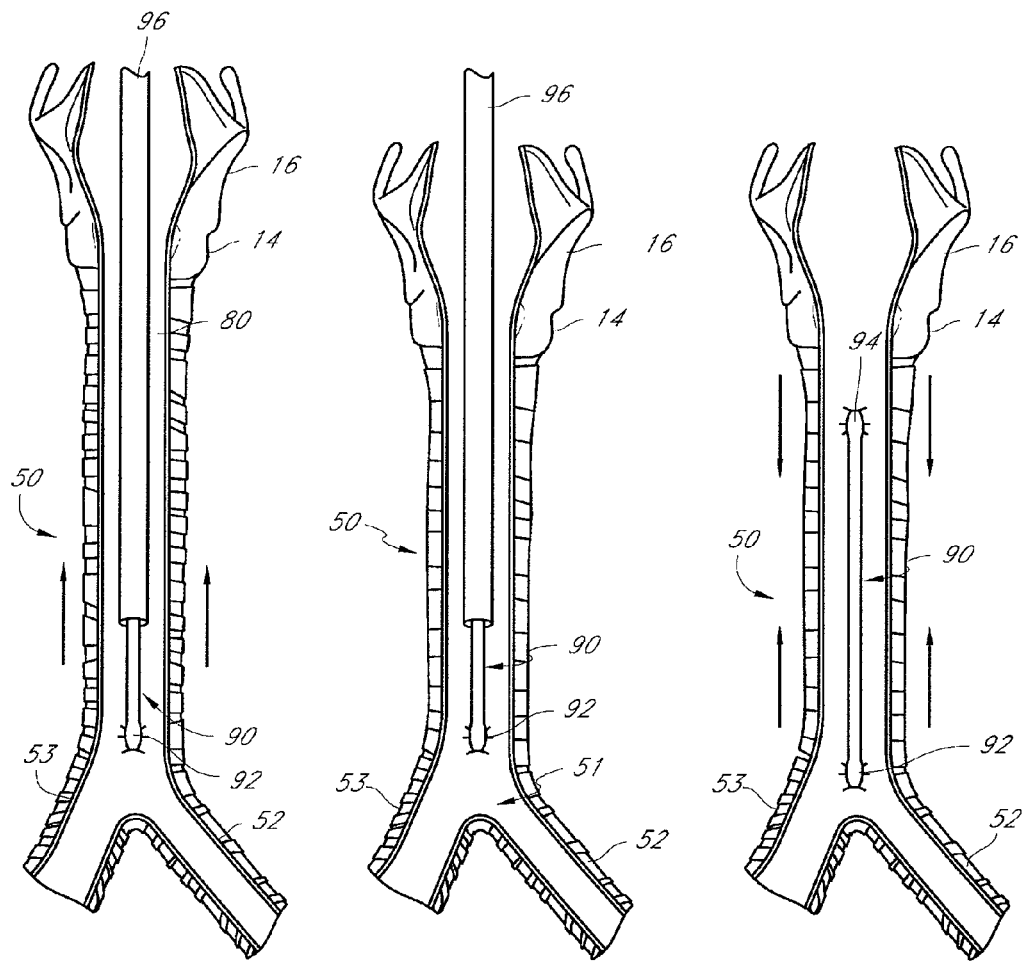
FIGS. 9A through 9C represent one embodiment of the invention comprising a fixed length implant for manipulating the trachea.

In FIGS. 9A through 9C, one embodiment comprises an elongate member 90 with a fixed length. At least one end 92 of the member 90 is first engaged to a body structure so that force can be applied to the member 90 to manipulate the trachea 50. In one embodiment, the distal end 92 of the elongate member 90 is attached to an inferior portion of the trachea 50. A superior force is then applied to the partially attached elongate member 90 to cause longitudinal compression of the trachea 50 superior to the insertion site. The remaining end 94 is then engaged to a superior portion of the trachea 50 to secure the tracheal manipulation. The elongate member 90 is then released from the delivery device 96.

Figure 10A:
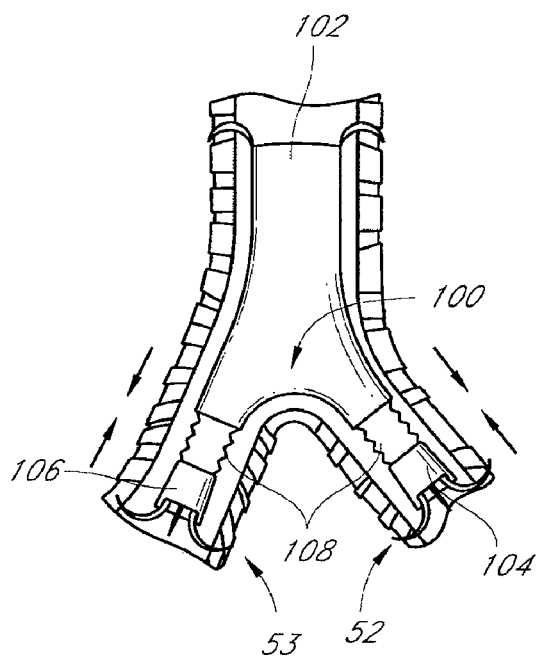
FIGS. 10A and 10B illustrate one embodiment of the invention comprising a bifurcated tubular configuration.
Figure 10B:
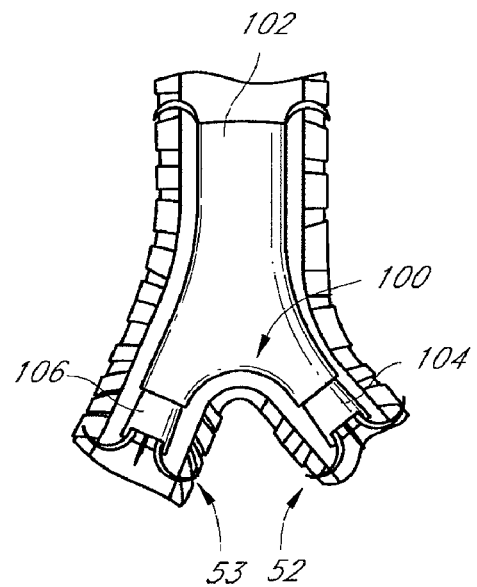

In one embodiment, the invention comprises a tubular member with a lumen to provide airflow through the tubular member. In one embodiment the tubular member comprises a series of connected rings. The proximal and distal ends of the tubular member are adapted to engage the inner surface of the respiratory tract along at least one diameter. In a further embodiment of the invention, shown in FIGS. 10A and 10B, the tubular member 100 comprises one proximal end 102 and two distal ends 104, 106 wherein the two distal ends 104, 106 are adapted to engage left and right mainstem bronchi 52, 53. The distal ends 104, 106 are connected to the proximal end 102 of the tubular member 100 by movable members 108 that are capable of forming an interference fit or a mechanical interfit with the rings of the tubular member such that the movable members 108, when pulled into the tubular member 100, are capable of resisting separation from the rings of the longitudinal member. In one embodiment, the movable member 108 comprises slidable tubing with corrugations capable of forming an interference fit. In one embodiment, the movable member comprises a suture or wire that can be drawn tight and fixed.

Figure 11A:
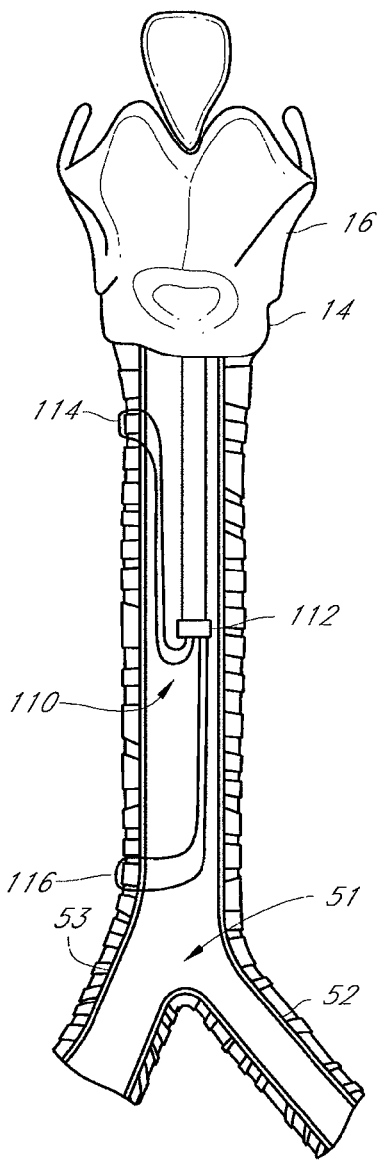
FIGS. 11A and 11B depict one embodiment of the invention comprising endoscopically placed sutures with a cinching member for securing the suture.
Figure 11B:
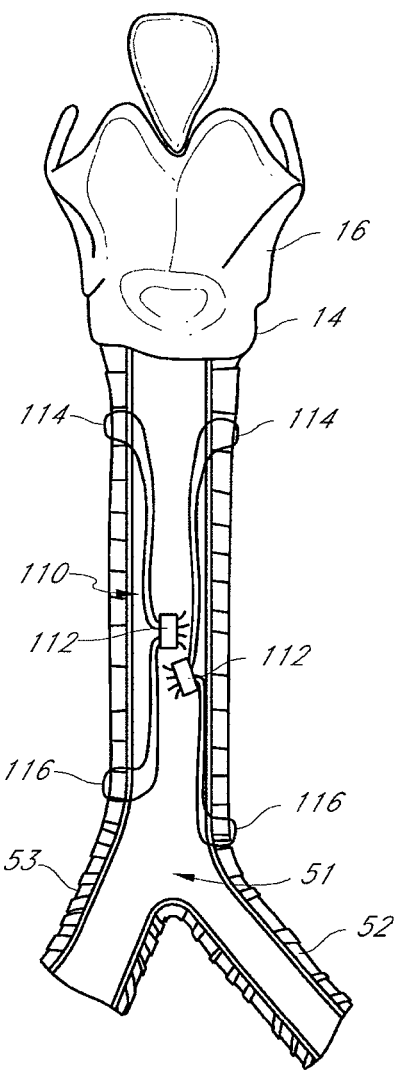

In still another embodiment of the invention, the device comprises at least one tracheal suture where the proximal end of the suture is engaged to a superior portion of the trachea and the distal end of the suture is engaged to an inferior portion of the respiratory tract at about the carina or mainstem bronchi. In one embodiment, illustrated in FIGS. 11A and 11B, the suture 110 is cinched by a cinching member 112 to bring the two suture ends 114, 116 closer together, thereby shortening the trachea 50. In another embodiment, the suture 110 is cinched using endoscopic knot pushers known in the art. The suture 110 is then secured to resist separation of the suture ends 114, 116. In another embodiment, at least one distal 114 end of the suture is placed within the inferior portion of the trachea or mainstem bronchi. Force is applied superiorly to the attached suture to longitudinally shorten the trachea and the proximal end of the suture is secured to a superior portion of the respiratory tract. In one embodiment, the suture or sutures are placed manually by the surgeon in an open surgical procedure. In another embodiment, the suture or sutures are placed endoscopically.

One skilled in the art will understand that the devices previously described may also be configured for placement on the external surface of the trachea. In one embodiment, the proximal and distal ends of at least one elongate member are engaged to the external tracheal wall to cause shortening of the trachea. FIGS. 12A and 12B depict one example of an external tracheal device comprising at least one helical spring 120. A tracheal manipulation device placed on the external surface of the trachea may be placed through a surgical site at the anterior neck, or through a thoracotomy or thoracostomy site into the chest cavity. Such approaches are further described below.

Figure 13:
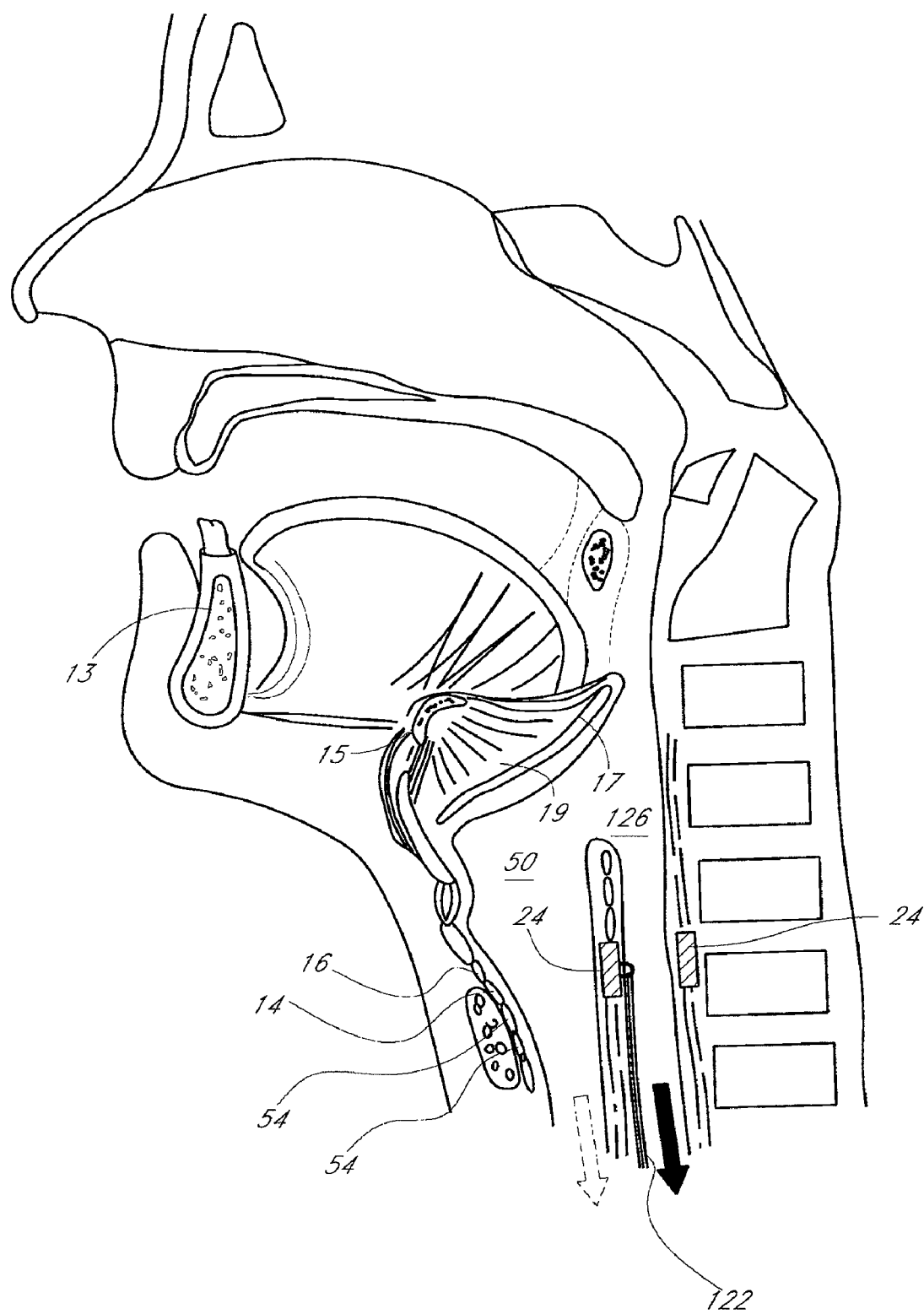
FIG. 13 depicts one embodiment of an esophageal implant in a schematic sagittal view through the hypopharynx, trachea and esophagus.

One skilled in the art will understand that the devices previously described may also be configured for attachment to structures adjacent to the trachea, including but not limited to the esophagus and gastro-esophageal junction. In one embodiment, the connective tissue between the respiratory tract and the gastrointestinal tract may be utilized to indirectly affect the trachea. By reconfiguring tissue adjacent to the trachea, the connective tissue attached to the trachea can develop tension and favorably displace or tighten the trachea. In one embodiment of the invention, an airway manipulation device is placed in the esophageal lumen. By taking advantage of the attachment between the trachea and esophagus through the membranous trachea and/or other fascial tissue, the airway may be manipulated indirectly. In some embodiments of the invention, indirect airway manipulation is preferred, to reduce the risk of airway stenosis. In a further embodiment of the invention, airway manipulation is performed with devices that affect the lateral and/or posterior walls of the esophagus. In some embodiments of the invention, avoiding attachment to the anterior wall of the esophagus may reduce the risk of forming a tracheoesophageal fistula. FIG. 13 depicts one embodiment of the invention involving indirect tracheal manipulation using an esophageal implant 122. The superior end 124 of the implant 122 is engaged to the wall of the esophagus 126 while the inferior end of the implant 122 is anchored to an inferior structure such as the inferior esophagus or gastroesophageal junction. Tension created between the superior and inferior ends of the esophageal implant 122 provides an inferior directed force to a portion of the esophagus 126, which in turn will also indirectly apply an inferior directed force to the trachea 50. Indirect manipulation of the trachea 50 or airway may be advantageous to reduce aspiration risk from the implant 120 and during device implantation. Indirect tracheal manipulation may also reduce the risk of tracheal necrosis and/or tracheal stenosis. An esophageal implant may also increase tension to the posterior pharyngeal wall, thereby treating sleep apnea through an additional mechanism independent of tracheal manipulation, although the invention is not bound by the mechanisms described.

In another embodiment of the invention, at least one end of the longitudinal member is attached to a portion of the airway while another end is attached to a non-airway structure, such as a clavicle, manubrium, sternum or rib. A longitudinal member that is partially attached to a non-tracheal structure may be advantageous for providing a more stable structure for exerting greater force on the trachea, or for applying force in particular directions not achievable by attaching a longitudinal member solely to the trachea or respiratory tract.

Figure 14A:
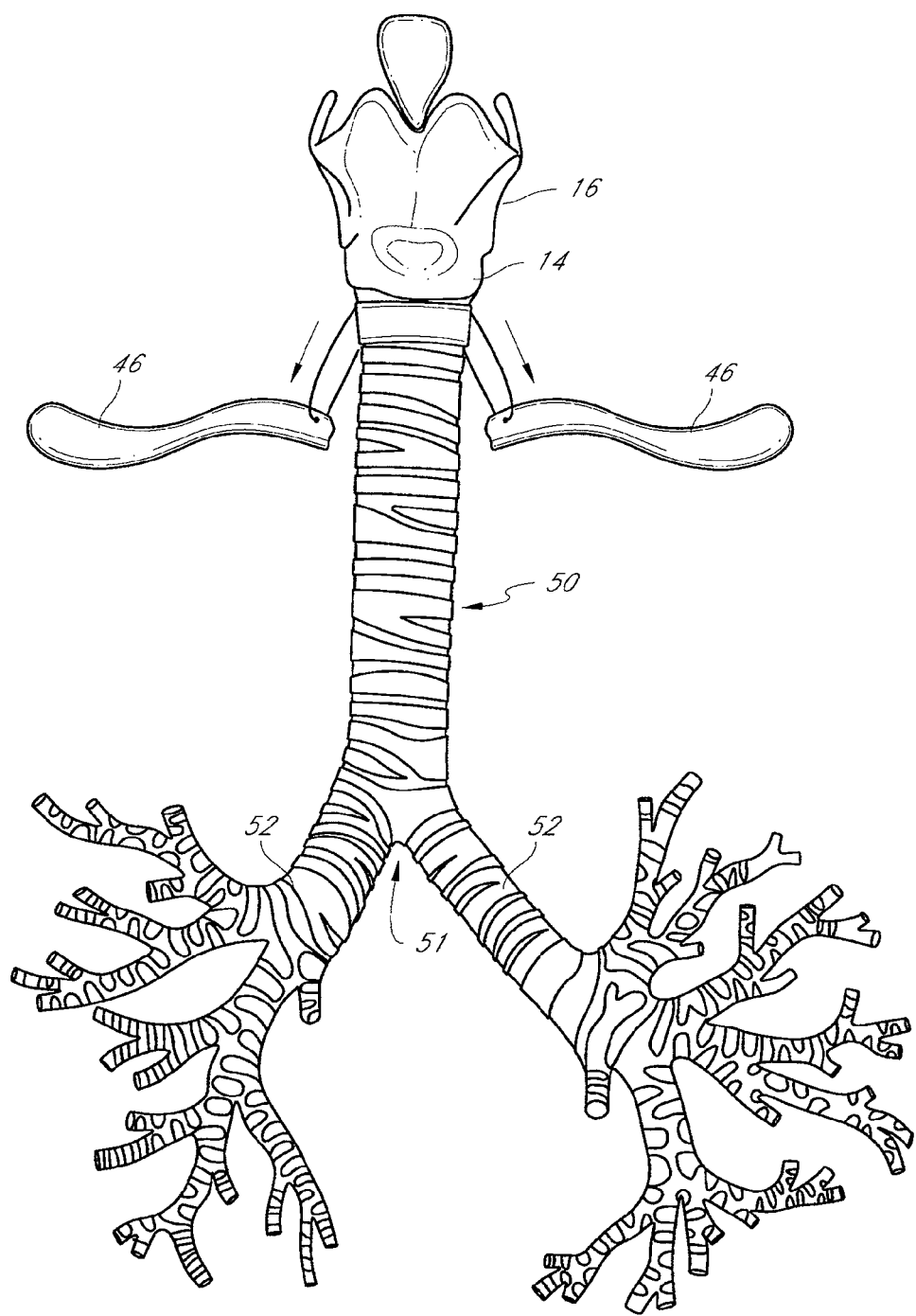
FIGS. 14A and 14B show one embodiment of the invention wherein the trachea is tensioned inferiorly by attachment to an anatomical structure such as the clavicles.
Figure 14B:
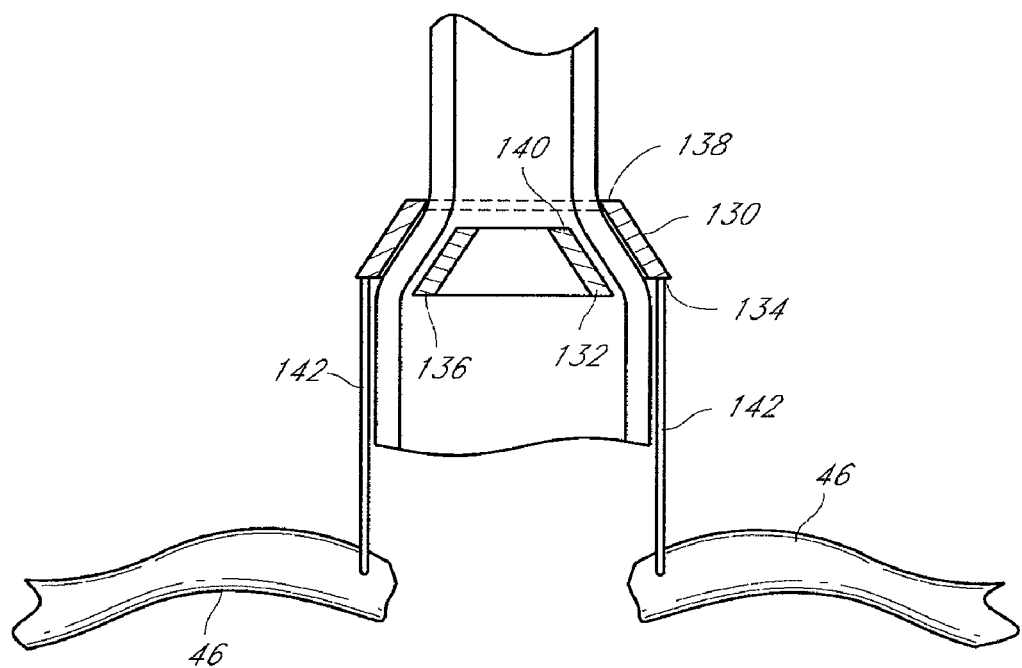

FIGS. 14A and 14B show one embodiment of the invention utilizing attachment to a non-tracheal or non-airway structure. The invention comprises two arcuate bodies 130, 132 for engaging the tracheal wall between the two arcuate bodies 130, 132. An inner arcuate body 132 is placed endotracheally while an outer arcuate body 130 is adapted for placement on the external surface of the trachea 50. The two arcuate bodies 130 132 having a C-shape configuration where the proximal ends 134, 136 of the bodies 130, 132 are wider than the distal ends 138, 140 of the bodies 130, 132, such that the arcuate bodies 130, 132 are capable of wedging the trachea between them when the inner arcuate body is inserted to about the same level of the trachea as the outer arcuate body. In other embodiments, at least one barb or hook on at least one arcuate body is capable of engaging the tracheal wall. In another embodiment, at least one barb or hook is capable of piercing the tracheal wall and engaging the other arcuate body to manipulate the trachea. The outer arcuate body 130 is further adapted for attachment of a suture 142, which can be used to anchor the trachea wedged between the two arcuate bodies 130, 132 to another body structure such as the clavicles 46, manubrium or sternum for displacing the trachea inferiorly. FIG. 14A depicts the outer arcuate body attached to the trachea, while FIG. 14B is a cross-sectional schematic view of the relationship between the outer arcuate body and the inner arcuate body with respect to the trachea. In another embodiment, only an outer arcuate ring is provided. In this embodiment, the outer arcuate ring is capable of engaging the external tracheal wall without requiring an endotracheally placed inner arcuate ring.

Figure 15A:
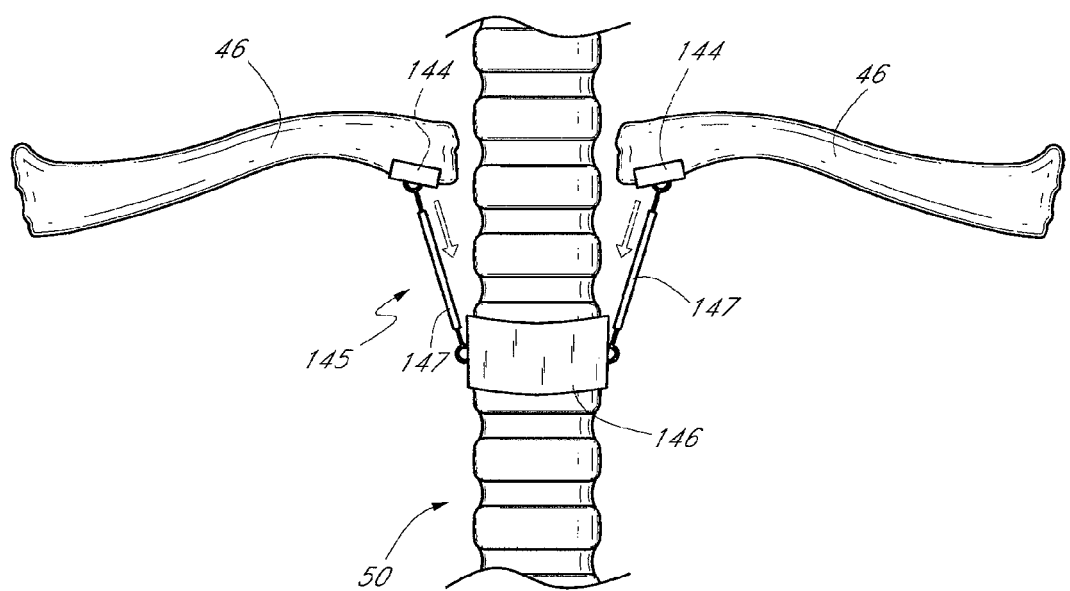
FIGS. 15A and 15B illustrate embodiments of the invention wherein the trachea is tensioned inferiorly by pushing against an anatomical structure such as the clavicles.
Figure 15B:
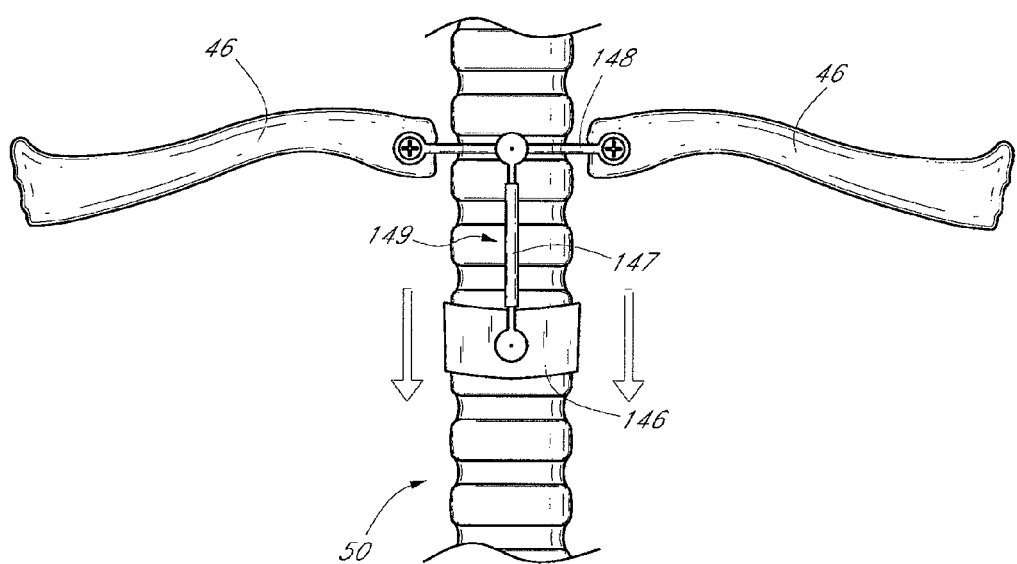

In an alternate embodiment of the invention, the device comprises a longitudinal member having a body, proximal end and distal end, wherein the body is capable of generating a separating force between the proximal end and distal end. FIG. 15A illustrates the proximal ends 144 of a longitudinal member 145 attached to a clavicle 143 and the distal end 146 is attached to an inferior portion of the trachea 50. A separating force is generated and the distance between the proximal ends 144 and distal end 146 is increased, thereby pushing the trachea 50 inferiorly. The separating force may be generated from a fixed length longitudinal member by distracting the trachea inferiorly prior to attaching the distal end of the longitudinal member. Optionally, the separating force may be generated from a dynamic, adjustable source such as an air piston 147. A dynamic source will allows some relative movement between the proximal and distal ends of the longitudinal member 145. Relative movement may provide greater comfort to the patient and decrease any impact of tracheal tension on swallowing compared to a fixed length implant. In still another embodiment shown in FIG. 15B, the proximal end 148 of the longitudinal member 149 comprises a cross bar adapted to engage both the right and left clavicles 143.

Figure 16A:
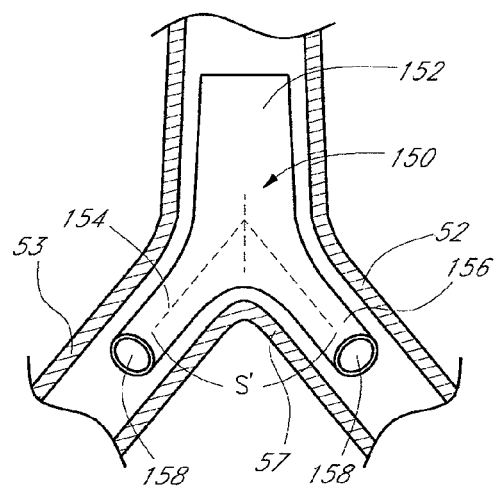
FIGS. 16A and 16B show one embodiment of the invention for altering the angle between the left and right mainstem bronchi.
Figure 16B:
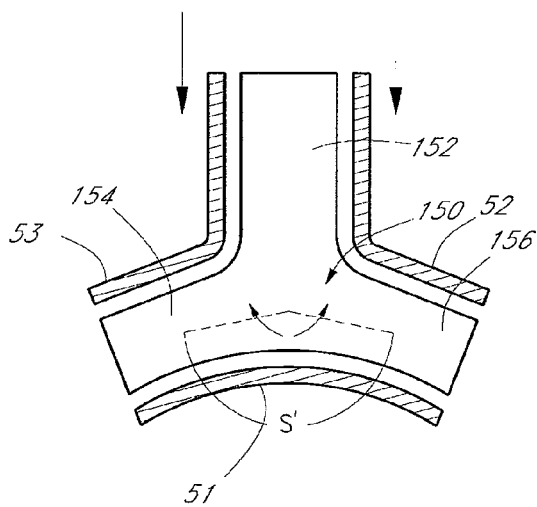

FIGS. 16A and 16B illustrate another embodiment of the invention for manipulating the airway. In one embodiment, the Y-shaped support 150 comprises a bifurcated stent with primary 152, first arm 154 and second arm 156 segments that contain lumens 158 that provide airflow through the support 150. The primary segment 152 is adapted for positioning about or within the carina 51 and/or airway and the first and second arm segments 154, 156 are adapted for positioning about or within the right and left mainstem bronchi, 53, 52 respectively. The support may further comprise a lining or sleeve 160 made from ePTFE or any of a variety of biocompatible linings capable of attachment to the support 150. Attachment of the lining 160 may be performed with adhesives, heat bonding, suturing or any of a variety of attachment methods known in the art.

The implant 150 is adjustable from a first orientation in which the first and second arm segments 154, 156 are separated by a first angle S, and a second configuration in which the first and second arm segments 154, 156 are separated by a second, wider angle S'. The device is configured to retain the second angle S'. By widening the angle S between the first and second arm segments 154, 156, the lung tissue surrounding those portions are displaced in a superior-lateral direction. This allows the bronchial tree to displace inferiorly, thereby putting inferior direction traction on the trachea 50. The angular change between the first and second positions will be a function of the desired clinical result for a given patient. In general, however, the second angle will be at least about 5 degrees or 10 degrees, and often at least about 20 degrees or 30 degrees greater than the first angle. By widening the angle formed between the mainstem bronchi 52, 53, the trachea 50 may be displaced inferiorly with respect to the lungs and thoracic cavity, thereby manipulating tracheal positioning or tracheal wall characteristics.

In one embodiment, the support 150 comprises a plastically deformable support 150 inserted bronchoscopically to the carina 51 and deformed with operator-applied deformation force using any of a variety of bronchoscopically manipulable tools known in the art. Such a support may comprise stainless steel, titanium and others known in the art. In one embodiment, the support comprises a shape memory material such as Nitinol that is inserted into the body in a first contracted configuration and assumes a second original configuration upon exposure to body heat that alters the relationship between the right and left mainstem bronchi. In another embodiment, the primary segment 152 and arm segments 154, 156 are attached by a joint or other articulation for facilitating change between the first configuration and second configuration. The joint may be a hinge joint, socket joint or any other joint capable of movement. In one embodiment, the support may further comprise a configuration lock for securing the arm segments in the first and/or second configurations. In one embodiment, the configuration lock comprises at least one suture for fixing the spatial relationship between the arm segments. In another embodiment, the configuration lock comprises a rotatable screw mechanism.

The carinal implant 150 may also be enlargeable from a first, reduced cross section to facilitate endotracheal navigation, and a second, enlarged cross section for positioning within the bifurcation. The support 150 is capable of passing through the oropharynx and larynx to the carina 51 of the trachea 50 by using a catheter, bronchoscope or other delivery system.

Figure 17A:
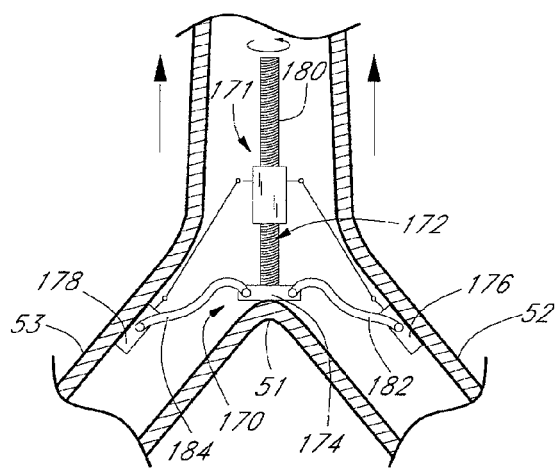
FIGS. 17A and 17B show another embodiment of the invention for altering the angle between the left and right mainstem bronchi.
Figure 17B:
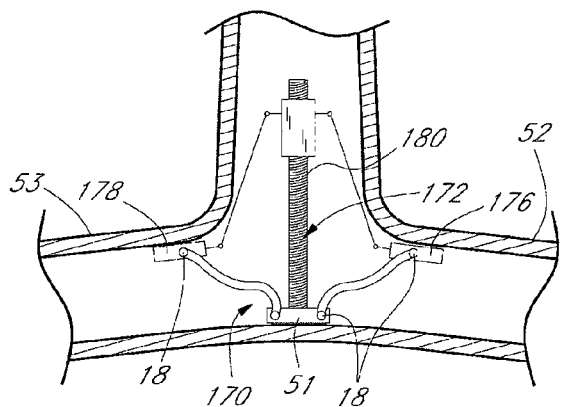

In another embodiment, shown in FIGS. 17A and 17B, the support 170 comprises a bar or wire frame 172 that lacks a lumen. The distal end 174 of the primary segment 180 and distal ends 176, 178 of the arms segments 182, 184 may have an increased surface area to reduce the risk of broncho-tracheal tissue necrosis resulting from the exertion of force. The distal ends 174, 176, 178 may have a curved or angled contact surface with the airway to reduce focal airway pressure that may cause necrosis. Changes to the relative position between the primary segment 180 and the arm segments 182, 184 may occur through deformation of the prosthesis, or facilitated by joints 186 located between the segments 180, 182, 184. Joints 186 may also be provided between the arm segments 182, 184 and their distal ends 176, 178, respectively. In one embodiment, a rotatable mechanical assembly 171 allows adjustment and fixation the arm segments 182, 184 positions with respect to the primary segment 180. Knotted sutures between the segments 180, 182, 184, or other fixation devices known in the art may also be used to fix the device configuration. The rotatable mechanical assembly 171 may have an anchor system for maintaining the position of the support and to prevent distal displacement of the support 170 into the bronchial tree. The anchor system may comprise a stent, inflatable cuff or one or more wall attachments.

Figure 18A:
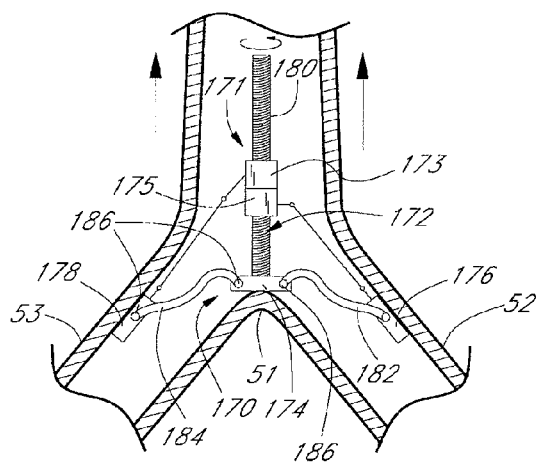
FIGS. 18A and 18B depict another embodiment of the invention for altering the angle between the left and right mainstem bronchi.
Figure 18B:
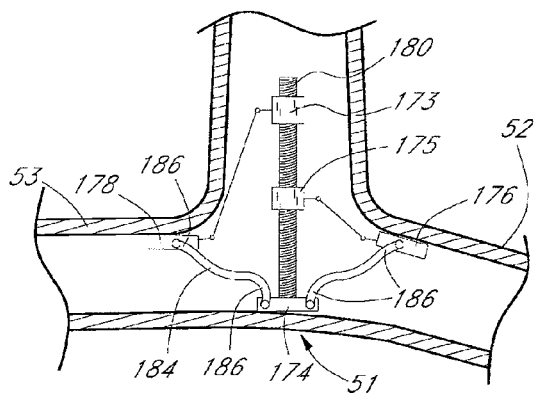
Figure 19A:
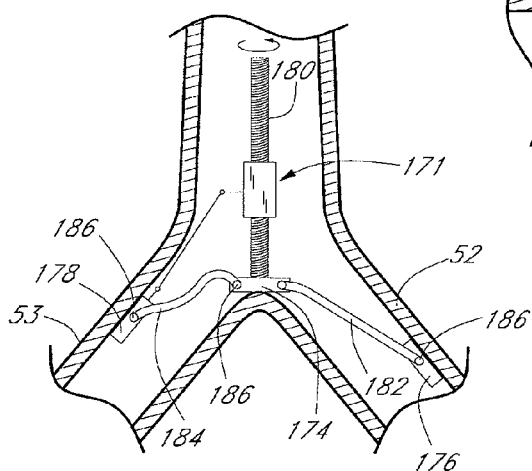
FIGS. 19A and 19B represent one embodiment of the invention for altering the angle of one mainstem bronchi.
Figure 19B:
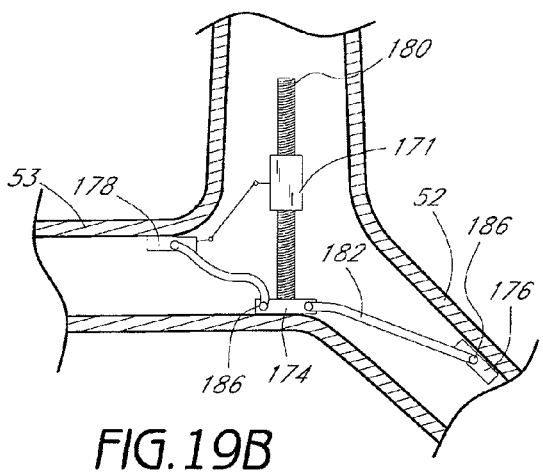

In another embodiment of the invention, the angles between each mainstem bronchi 52, 53 and the trachea 50 are separately adjustable. This embodiment allows one adjustable angle of the device to be adjustable independent of the other angle relative to the primary segment. FIGS. 18A and 18B depicts a support 170 where the first arm segment 184 and second arm segment 182 are configurable to different positions with respect to the primary segment 180 through separate rotatable mechanical interfaces 173, 175. In another embodiment, shown in FIGS. 19A and 19B, only one angle between the first arm segment 184 and the primary segment 180 is adjustable while the other angle between the second arm segment 182 and the primary segment 180 is fixed. In one embodiment, the length of the second arm segment 182 may be significantly longer than the first arm segment and have a greater angle with respect to the primary segment 180 to reduce to overall insertion profile of the support 170 into the airway.

Figure 20A:
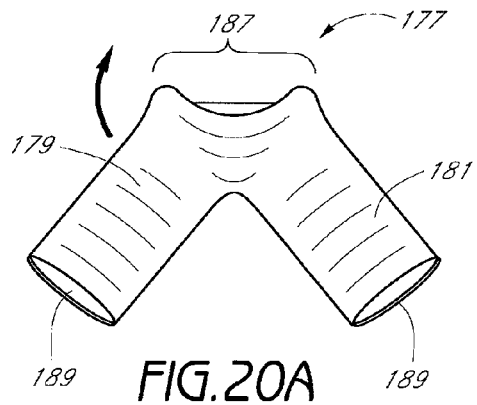
FIG. 20A is a side elevational view of a two-segment airway remodeling stent.
Figure 20B:
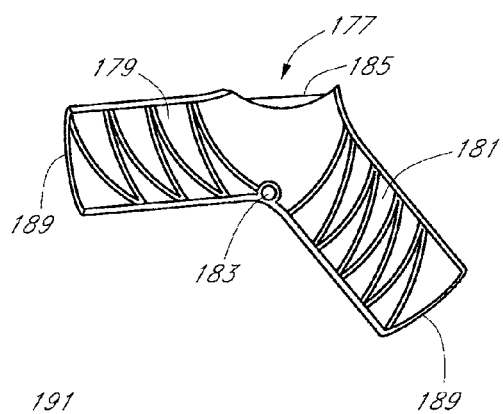
FIG. 20B is cross sectional view of the stent from FIG. 20A.

FIGS. 20A and 20B depict another embodiment of the invention comprising a two-segment tubular airway stent 177. The stent is adapted for insertion into the airway of a patient generally about the carina 51 and is capable of reorienting the relative positions of the airway about the stent 177. The stent 177 comprises a first tubular segment 179 and a second tubular segment 181 connected by a movable joint 183 and a fixation assembly 185 for securing the relative position between the first tubular segment 179 and second tubular segment 181. This embodiment of the invention lacks a primary segment adapted for positioning within the trachea but provides an opening 187 in the device to provide the passage of air between the opening 187 and the ends 189 of the device. As shown in the cross sectional view in FIG. 20B, each tubular segment 179, 181 may be configured with a zig-zag structure, lattice structure, or any of a variety of stent-like configurations. The stent may be self-expandable upon release from its delivery tool, or the device may require application of external force, such as a balloon catheter, to expand. The configuration of each tubular segment 179, 181 need not be the same. One skilled in the art can dimension the device 177 based upon the particular anatomy of a patient. The joint 183 may be a hinge joint as shown in FIG. 20B, or a ball-and-socket joint, or any interface between the two segments 179, 181 that allow the device 177 to remodel the surrounding airway. The stent segments 179, 181 need not be distinct in structure with respect to each other, thus the joint 183 or joints may include but are not limited to one or more deformable struts or links between the two segments 179, 181 that are similar in structure to the other portions of the stent 177. The fixation assembly 185 may comprise any of a variety of fixation structures capable of securing the relative position of the two segments. The fixation assembly may comprise a suture attaching the two segments, as shown in FIG. 20B, or a set screw or lynch-pin type of fixation component.

Figure 21A:
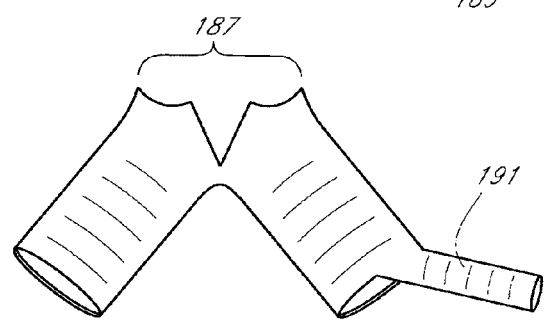
FIGS. 21A through 21C depict one embodiment of a three-segment airway remodeling stent.
Figure 21B:
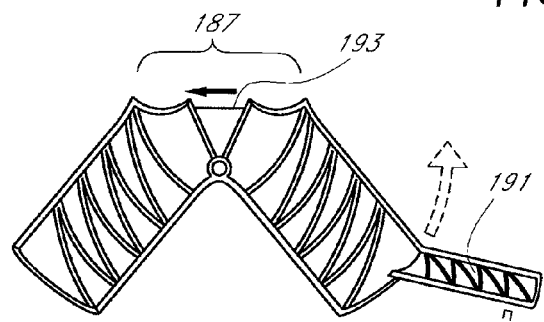
Figure 21C:
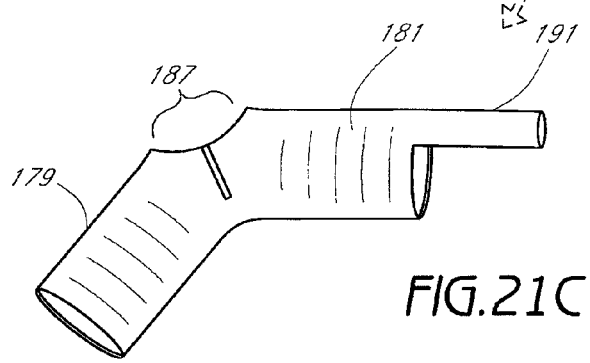

In another embodiment, shown in FIGS. 21A through 21C, the airway remodeling stent 177 further comprises one or more branch segments 191 adapted to insert into more distal branches of the airway. The branch segments 191 allow remodeling of the airway into the distal portions of the lungs and may be beneficial in redistributing the remodeling force through a greater portion of the bronchial tubes or lungs. Each segment need not be discreet from the other segment(s). In some embodiments, a multi-segmented stent may have a continuous, curved and/or tapering structure, where a "segment" refers generally to each portion of the stent separated by a branching point in the airway where the stent is configured for implantation. FIG. 21A depicts an airway remodeling stent 171 with a first mainstem segment 179, a second mainstem segment 181 and a first order branch segment 191 attached to the second mainstem segment 181. A variety of fixation assemblies may also be used for this embodiment of the remodeling device, but one preferred fixation assembly comprises a slidable wire 193 or suture along the length of a longitudinal curvature of the segments 181, 191 that, when tightened, causes the segments 179, 181, 191 to assume a different alignment. By altering the design of the fixation assembly, different reorientation effects may result. Between any two segments of a stent, creating tension in the slidable wire 193 may straighten the alignment between the two segments or increase the angle between two segments. A straightening alignment is shown in FIGS. 21A to 21C between one segment 181 and another segment 191. In a multi-segmented or branching stent, a combination of straightening and increased curvature or angulation may occur. One skilled in the art will understand that a remodeling stent may be designed to reorient to any desired configuration. This particular fixation assembly allows reorientation of the distal segment 191 of the device while not requiring access to the most distal segments of the bronchial tree. Any of a variety of mechanical or friction fits known in the art may be used.

Figure 22A:
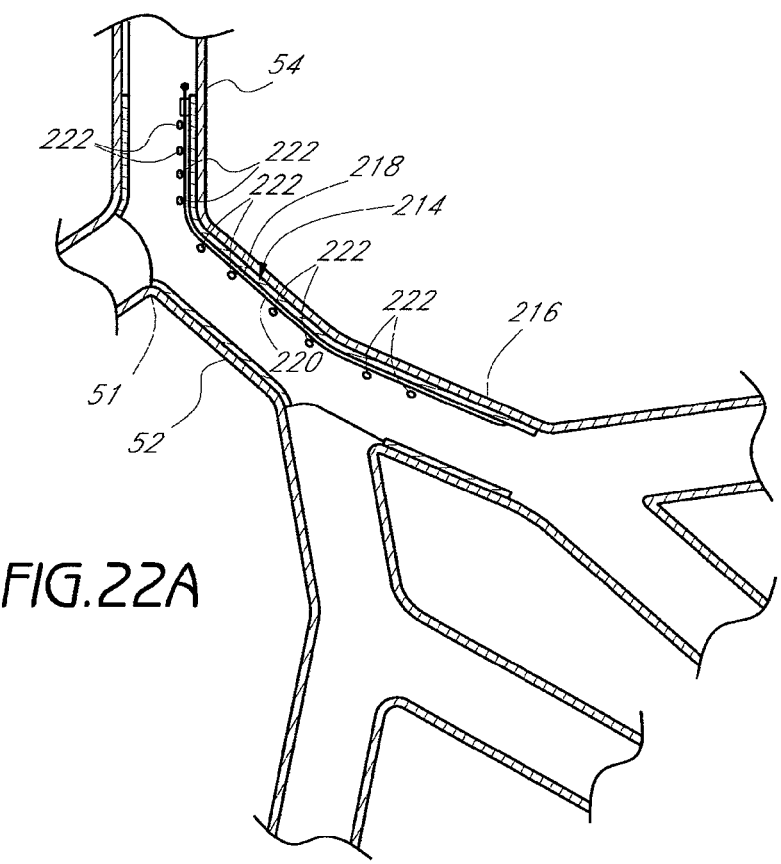
FIG. 22A depicts another embodiment of a three-segment airway remodeling stent in a first configuration.
Figure 22B:
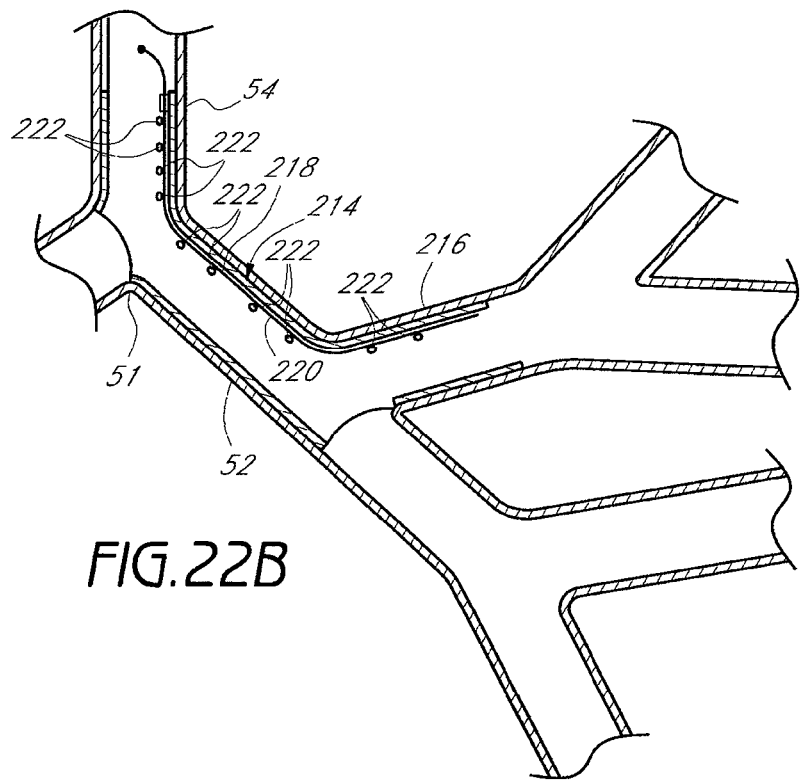
FIG. 22B depicts the remodeling stent of FIG. 22A following fixation.

Other embodiments of the invention may be configured for implantation in other portions of the airway. For instance, FIGS. 22A and 22B depict an embodiment comprising a multi-segmented stent 214 configured for implantation along as portion of the trachea, the left mainstem bronchi 52 and a branch of the mainstem bronchi 216. In this embodiment, the stent is designed with a fixation assembly 218 along the lesser curvature of stent 214 comprising a slidable tension wire 220 and one or more conduits 222 for restricting the sliding path for the tension wire 220. After implantation into the airway as illustrated in FIG. 22A, tension is applied to the slidable tension wire 220, causing an increase in the curvature of the stent 214. This increased curvature facilitates the displacement of the lung tissue in a lateral-superior direction and may further enhance concomitant inferior displacement of the trachea 54.

In still another embodiment of the invention, illustrated in FIG. 23A, the bronchoscopic stent comprises a unilateral stent 195 adapted for insertion into one side of the bronchial tree. The unilateral stent 195 may cross one or more bronchial branches areas 197, 199 within the bronchial tree and may comprise one or more contiguous or distinct segments. FIG. 23A depicts a three segment stent, comprising a proximal 201, middle 203 and distal segment 205. The unilateral stent 195 may be placed along any portion of the bronchial tree and need not include a segment residing in either mainstem bronchi 52, 53 but will typically include a mainstem bronchi segment for ease of access, manipulation and/or retrieval. One skilled in the art can select the dimensions of different portions of the stent 195 based upon the desired position within the bronchial tree. The multi-segmented stent 195 has an alignment system for altering and fixating the relationship between the segments of the stent. This alignment system 207 may include one or more hinges 209, a pull wire 211 along the length of the stent that is attached or anchored generally at a distal portion of the stent 195, and a restrictor 213 for fixing the wire position. By placing tension on the pull wire 211, the portions of the stent 195 are brought closer together and into a different alignment, which in turn can be fixed by a wire restrictor 213 that resist relief of the wire tension. The wire restrictor 213 may comprise a conduit that resists movement of a knot in the wire 211 through the conduit, or a one-way cinching member attached to the wire 211. Other alignment systems may also be used, including insertion of a stiffening structure, elastic deformation of the stent 195 back to its natural alignment or other system capable of altering the alignment of the stent segments. The alignment system need not affect the alignment of every segment of the device, as some segments may be used not for remodeling the bronchial tree but to resist collapse of the bronchial lumen in portions of the lung adjacent to remodeled portions. Referring to FIG. 23B, by altering the relative alignment of a portion of the bronchial tree, the lung material is displaced in an superior-lateral direction and allows the lungs to assume a more inferior position, thereby increasing the tension of the airway.

Figure 24A:
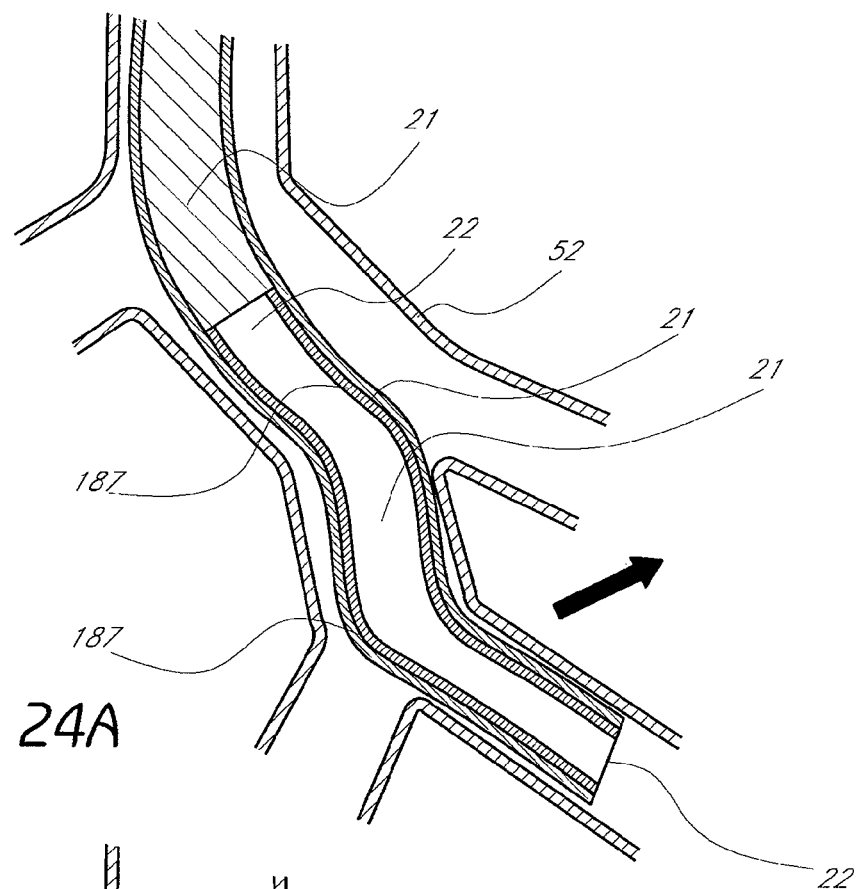
FIGS. 24A and 24B are cross sectional views of the deployment of one embodiment of a unilateral remodeling stent.
Figure 24B:
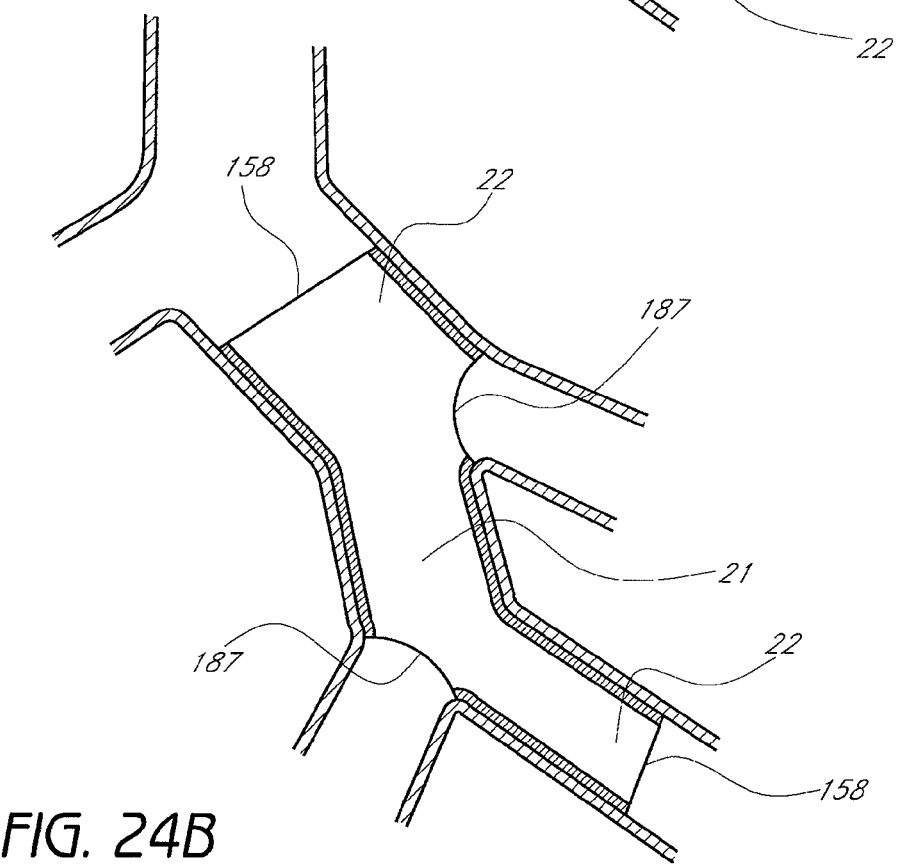

In one embodiment of the invention, the device is deformed from its inherent shape during the insertion of the device and reverts and realigns upon release from the delivery tool. FIG. 24A depicts a deformable remodeling stent 215 in its radially collapsed configuration within a delivery tool 217. The stent 215 comprises a metallic lattice structure with or without a jacket covering 219 and is capable of elastic deformation from its radially collapsed state and capable of exerting sufficient force upon expansion to remodel the surrounding bronchi and pulmonary tissue. Lumens 158 at the proximal end 221 and distal end 223 allow airflow through the length of the stent 215. Side openings 187 are provided in the side wall of the stent 215 to allow airflow to and from bronchial branches adjacent to the stent 215. Other stent configurations are known in the art and may be used in addition to a lattice structure. The stent 215 may have radio-opaque markers visible on radiography or fluoroscopy, or indicia visible during bronchoscopy to facilitate positioning of the stent 215 with respect to the adjacent branches. FIG. 24B depicts the stent deployed in the left mainstem bronchi having repositioned the pulmonary tissue to allow inferior displacement of the trachea.

Figure 25A:
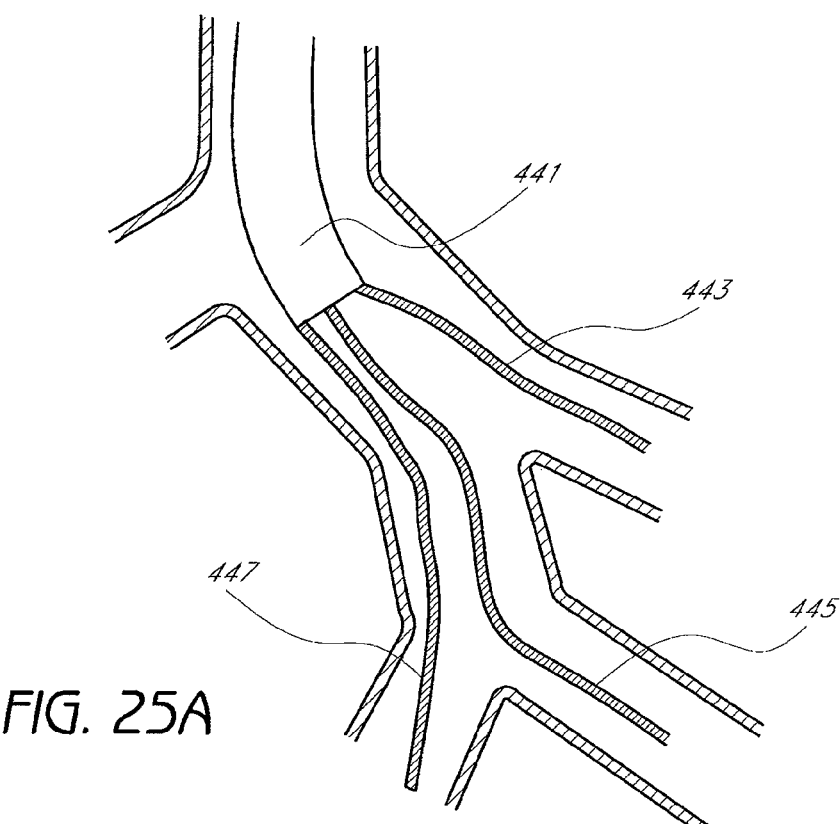
FIGS. 25A and 25B are cross sectional views of the airway during deployment of a branched remodeling stent.
Figure 25B:
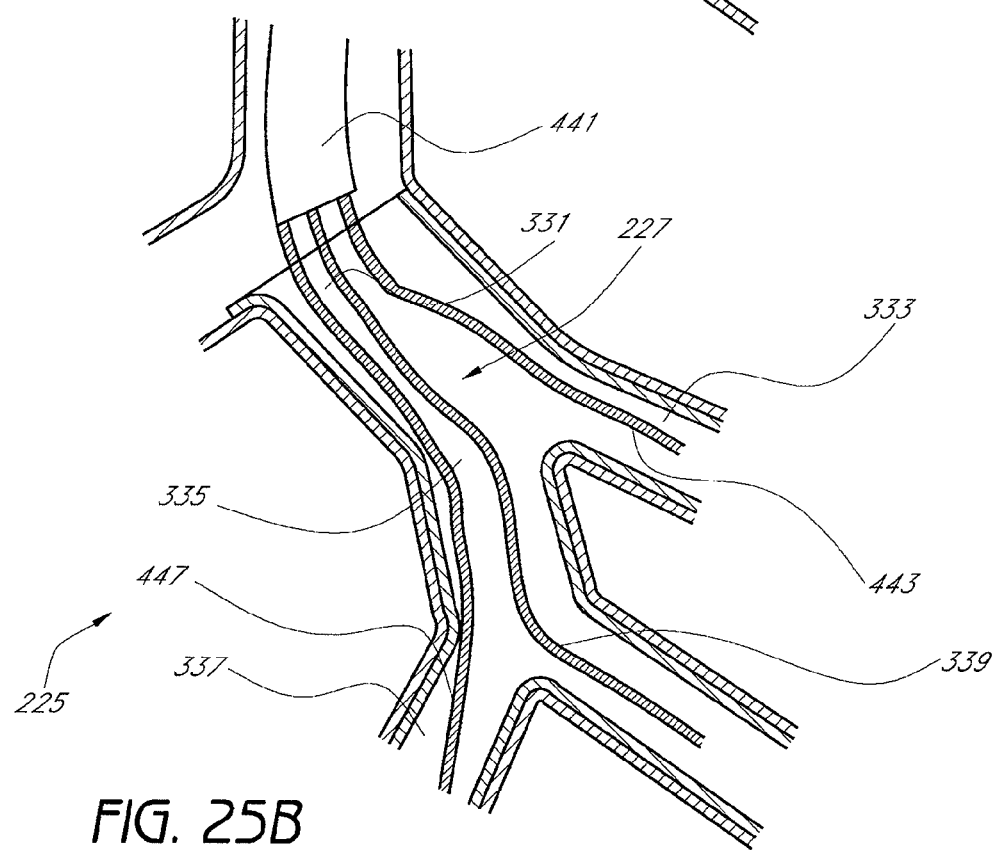

The remodeling stent may have a branching or serial configuration. A serial configuration is depicted in FIGS. 24A and 24B. In a serial configuration, the portions of the stent are generally arranged in an end-to-end fashion. Referring to FIG. 25B, one embodiment of the invention comprises a remodeling stent 225 with a branching configuration, where the stent 225 has at least one joint area 227, 229 where three or more portions (331, 333, 335 and 335, 337, 339) of the stent 225 generally attach. The three portions need not converge at exactly the same point, but only in the same general area sufficient to position the segments at a portion of the bronchial tree and the branches of that portion. As mentioned previously, a branching configuration may enhance the remodeling effect on lung structure, and/or may be beneficial in preserving patency of adjacent bronchial lumen with remodeling, compared to a serially configured remodeling stent. In one embodiment of the invention, a method for implanting a branched remodeling stent is provided. Referring to FIG. 25A, the method comprises inserting a bronchoscopy delivery tool 441 into the airway of a patient and passing one or more guidewires 443, 445, 447 into one or more branches of the bronchial tree where the stent 225 is to be inserted. Typically, a guidewire will be used for each distal branch where the branched remodeling stent is to be placed, but for some embodiments of the invention, the number of guidewires may be less. The remodeling stent is released from the delivery tool into the airway where is can self-expand or be expanded to cause remodeling of the pulmonary structures.

Figure 26A:
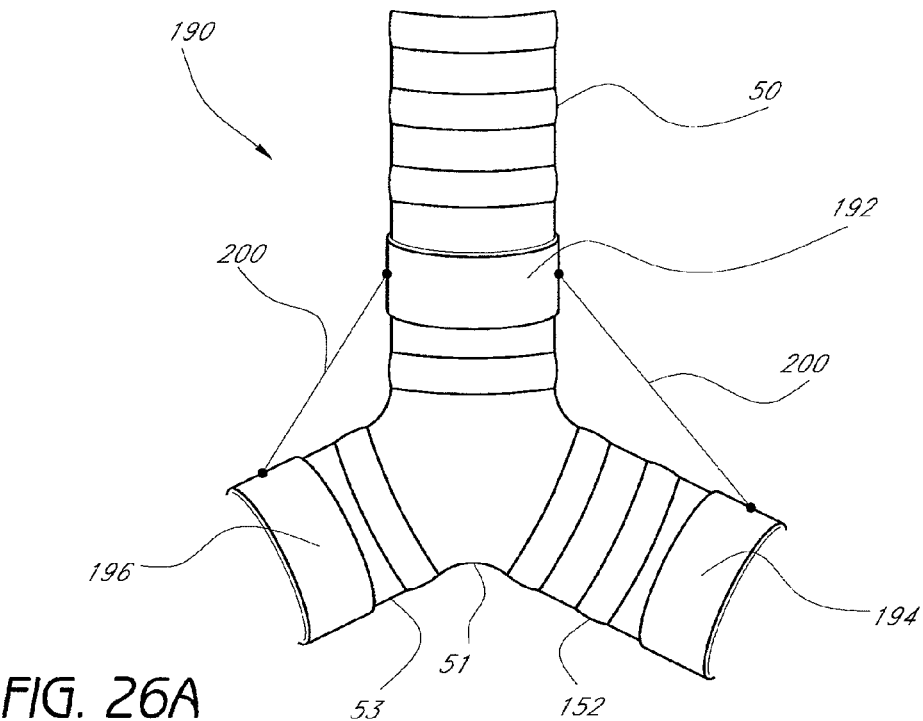
FIGS. 26A and 26B illustrate one embodiment of the invention for altering the angles of the mainstem bronchi.
Figure 26B:
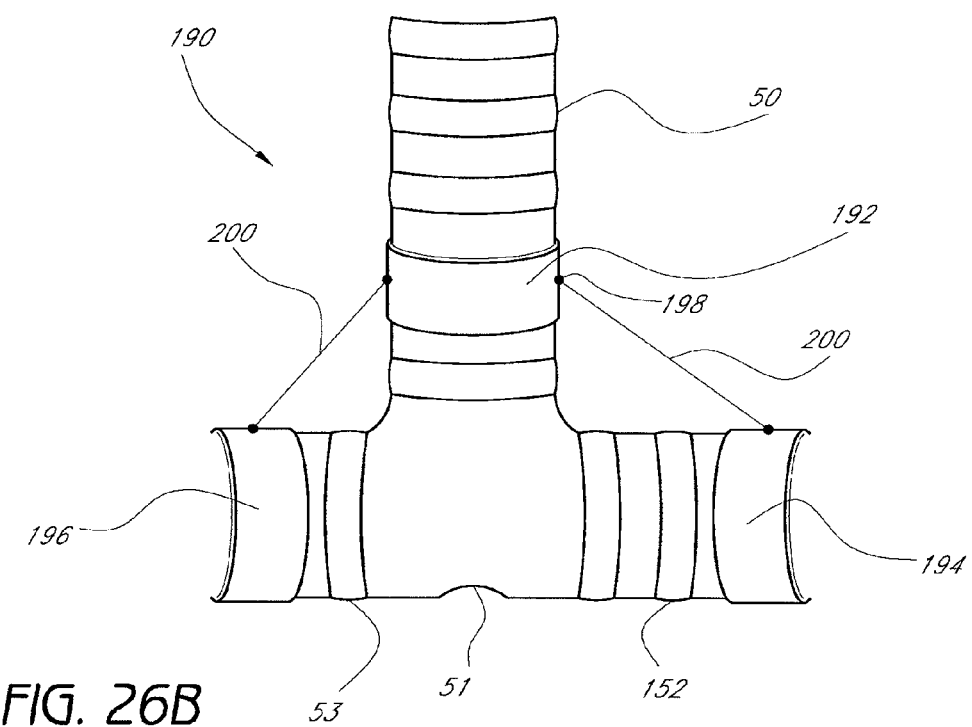
Figure 27A:
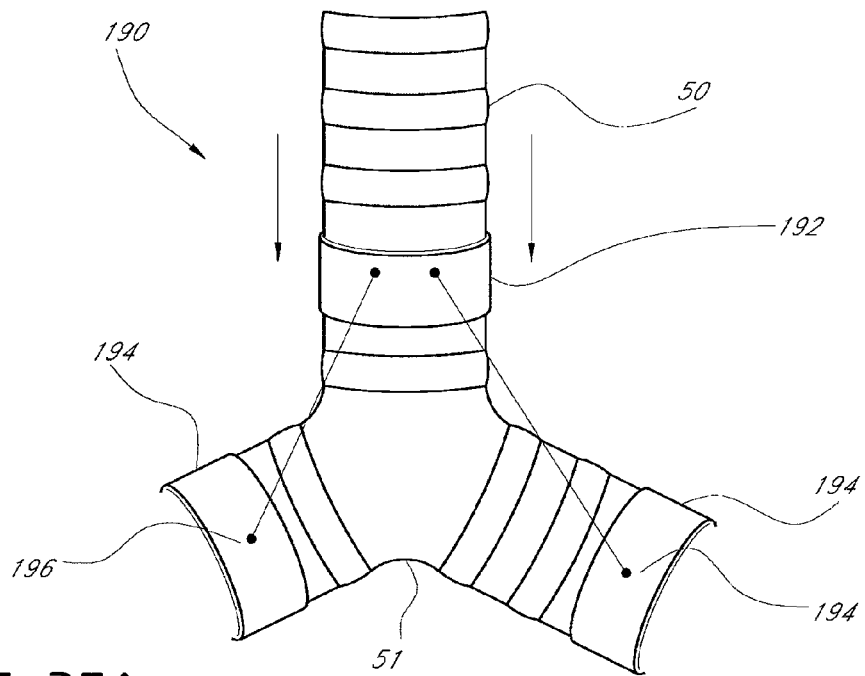
FIGS. 27A and 27B depict embodiments of the invention for pulling the trachea inferiorly toward the carina.
Figure 27B:
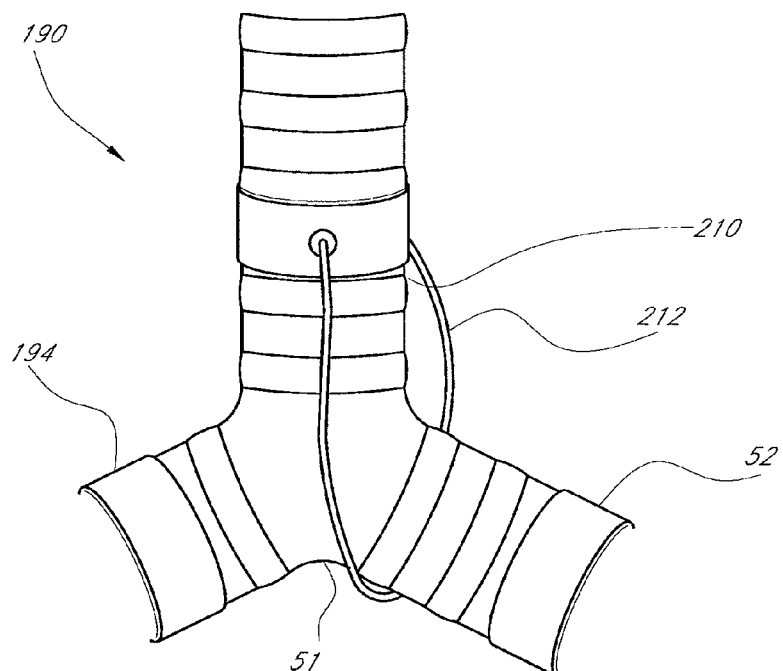

In another embodiment of the invention, illustrated in FIGS. 26A and 26B, widening the angle between the mainstem bronchi 52, 53 is performed by attaching an airway manipulation device 190 to the external surface of the trachea 50. In one embodiment of the invention, the airway manipulation device comprises at least three C-shaped clamps 192, 194, 196 adapted to engage the external surfaces of the trachea 50 and mainstem bronchi 51, 52. In one embodiment, each clamp has an aperture 198 for engaging a suture 200 such that when the sutures placed between the mainstem bronchi and the tracheal clamps 194, 196 are tightened, the mainstem bronchi 52, 53 are reoriented superiorly to cause the trachea 50 to displace inferiorly. FIG. 27A shows an embodiment that may also synergistically displace at least a portion of the trachea 50 generally about the C-shaped tracheal clamp 192 in an inferior direction, further enhancing tracheal manipulation. In another embodiment, shown in FIG. 27B, the invention comprises a proximal C-shaped clamp 210 without any distal C-shaped clamps. The suture, ribbon or cord 212 attached to the proximal clamp 210 may be wrapped around the carina 51 and tightened and reattached to the same clamp 192. This embodiment of the invention does not significantly alter the angle between the left 52 and right mainstem bronchi 53, but compresses the portion of the trachea 50 between the clamp 192 and the carina 51 to manipulate the portion of the trachea 50 superior to the clamp 192.

One skilled in the art will understand that any of a variety of clamps may be used to engage the respiratory tract, including but not limited to clamps that completely encircle the trachea or bronchi, malleable split rings or elastic split rings. In one embodiment, C-shaped rings are preferred to reduce the risk of necrosis that exists when a full circumference is dissected around a portion of the respiratory tract. Full circumference dissection has been known to disrupt the blood supply to that portion of the respiratory tract and cause necrosis.

Figure 28:
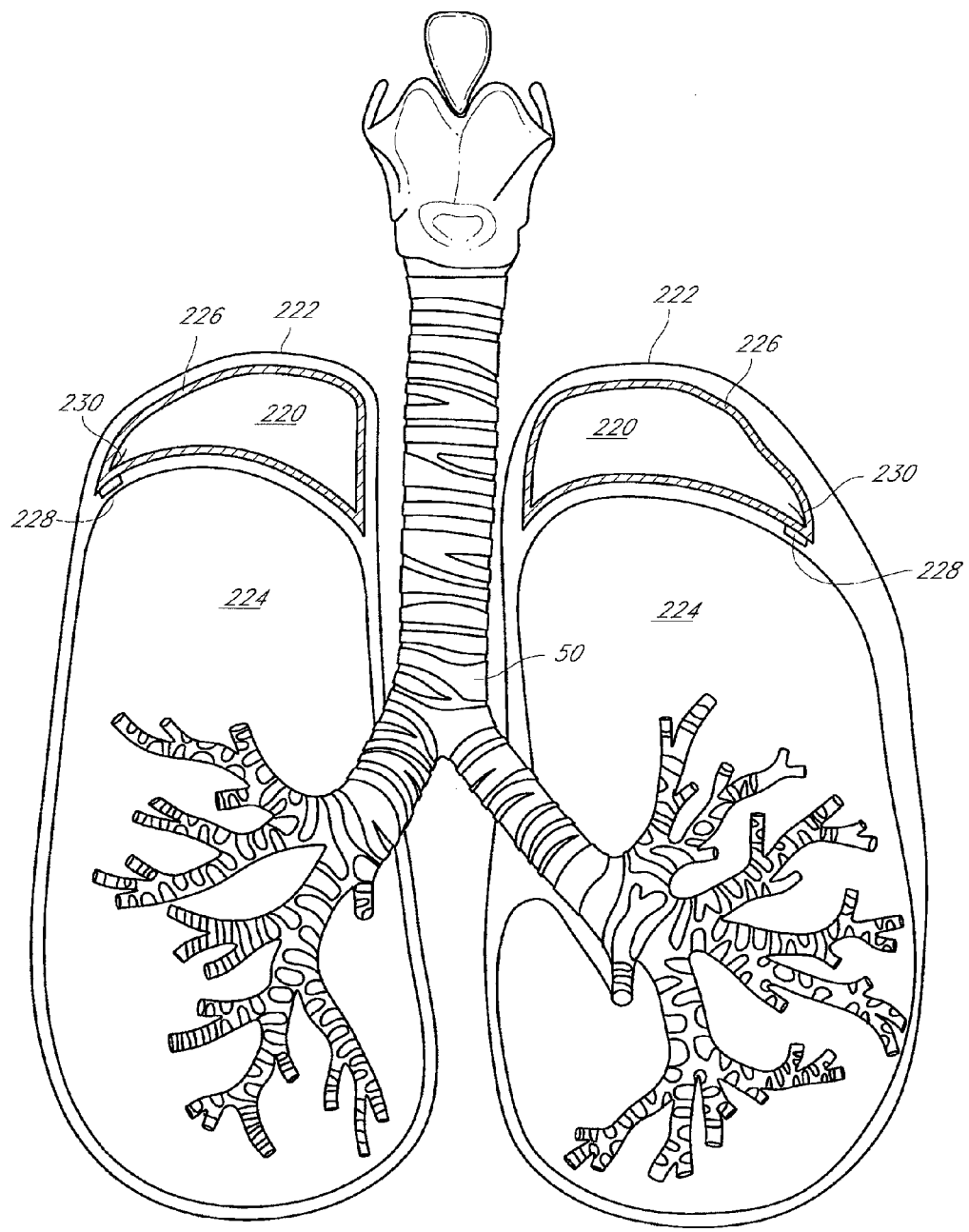
FIG. 28 depicts an embodiment of the invention for displacing the bilateral lungs inferiorly to manipulate the trachea.

FIG. 28 depicts one embodiment of the invention, comprising lung volume displacers 220 that are adapted for positioning in the apices 222 of the thoracic cavity. When positioned in the thoracic cavity, the displacers 220 can move the bilateral lungs 224 inferiorly, which in turn will displace the trachea 50 inferiorly. The lung volume displacers 220 may comprise an inflatable body 226 with an inflation port 228 and an attachment interface. The attachment interface can configured to engage a catheter, syringe or both. In one embodiment, the attachment interface comprises a female Luer adapter, but one skilled in the art will understand that any of a variety of detachment interfaces may be used. In one embodiment, the inflation port 228 further comprises a one-way valve 230 for limiting escape of inflation material from the inflation body and into the pleural space of the thoracic cavity. The volume displacers 220 may be filled with any of a variety of liquids, gaseous fluids or other media, including but not limited to helium, nitrogen, carbon dioxide, filtered room air, water, silicone curable foam or polymers or any other biocompatible materials known in the art. The volume displacers may be placed through a minimally invasive intercostal insertion site described below.

Any of a variety of alternative volume displacement structures may additionally be utilized in the manner described above. For example, volume displacing foams, with or without an outer flexible wall (e.g., a balloon or fabric bag) may be utilized. Self expandable mechanical structures, such as a Nitinol, stainless steel or other wire formed into a zig-zag configuration may be compressed for introduction superior to the lung in the thoracic cavity, and released to self expand under its own bias and displace the lung inferiorly.

For the embodiments discussed herein, the airway manipulation device, together with the other components of the present invention can be manufactured in accordance with any of a variety of techniques which are well known in the art, using any of a variety of medical-grade construction materials. For example, the airway manipulation device and other components of the present invention can be injection-molded, extruded or otherwise formed from a variety of medical-grade polymers including high or other density polyethylene, nylon, PEEK, PEBAX and polypropylene. Portions of the device can be separately formed and secured thereto in a post-molding operation, using any of a variety of securing techniques such as solvent bonding, thermal bonding, adhesives, interference fits, pivotable pin and aperture relationships, and others known in the art. In certain embodiments, the components of the tracheal manipulation device may be integrally molded, if the desired material has appropriate physical properties.

A variety of absorbable polymers may be useful for the formation of temporary implants, particularly in the case of extratracheal implants. Many of these polymers have been reported to be biodegradable into water-soluble, non-toxic materials which can be eliminated by the body: Polycaprolactone; Poly (L-lactide), Poly (DL-lactide); Polyglycolide; Poly (L-Lactide-co-D, L-Lactide) 70:30 Poly (L-Lactide-co-D, L-Lactide); 95:5 Poly (DL-lactide-co-glycolide); 90:10 Poly (DL-lactide-co-glycolide); 85:15 Poly (DL-lactide-co-glycolide); 75:25 Poly (DL-lactide-co-glycolide); 50:50 Poly (DL-lactide-co-glycolide); 90:10 Poly (DL-lactide-co-caprolactone); 75:25 Poly (DL-lactide-co-caprolactone); 50:50 Poly (DL-lactide-co-caprolactone); Polydioxanone; Polyesteramides; Copolyoxalates; Polycarbonates and Poly (glutamic-co-leucine).

The desirability of any one or a blend of these or other polymers can be determined through routine experimentation by one of skill in the art, taking into account the mechanical requirements, preferred manufacturing techniques, and desired reabsorption time. Optimization can be accomplished through routine experimentation in view of the disclosure herein.

The devices can be molded, formed or machined from biocompatible metals such as Nitinol, stainless steel, titanium, and others known in the art. Alternatively, the devices may further comprise a bioresorbable component to promote fibrosis and fixation of adjacent structures. One suitable bioabsorbable material which appears to exhibit sufficient structural integrity for the purpose of the present invention is poly-p-dioxanone, such as that available from the Ethicon Division of Johnson & Johnson. Poly (L-lactide, or co-DL-lactide) or blends of the two may alternatively be used. As used herein, terms such as bioabsorbable, bioresorbable and biodegradable interchangeably refer to materials which will dissipate in situ, following a sufficient post-operative period of time, leaving acceptable byproducts. Bodily reaction to the bioabsorbable materials or byproducts may furnish at least a portion of the support provided by the device or treatment method.

The device may also comprise a drug eluting component for treating any inflammation, infection, fibrosis or cellular proliferation that may result at the implantation site. In one embodiment of the invention, an endotracheal device with a drug eluting component may be used to resist the development of tracheal stenosis.

In one embodiment of the invention, a method for manipulating the airway is provided. A patient with sleep-disordered breathing is identified, at least a portion of the airway is accessed and the airway is manipulated. In one embodiment, the airway is manipulated by removal of at least one tracheal ring along with anastomosis of the two tracheal rings adjacent to the excised tracheal segment to shorten the trachea.

In another embodiment of the invention, a method for manipulating the airway is provided. The trachea is accessed, the portion of the tracheal tissue between the cartilaginous rings is shrunk and the trachea is shortened. The shrinkage of the tissue may be performed with any of a variety of tissue tightening methods known in the art, typically by activation of a thermal energy service such as cryotherapy, ultrasound, laser, microwave and/or radioablation, or a chemical method such as sclerotherapy.

In another embodiment of the invention, a method for manipulating the airway is provided. A patient with sleep-disordered breathing is identified, the thoracic cavity is accessed and the airway is manipulated. In one embodiment, manipulation of the airway is performed by reducing thoracic cavity volume in its apical regions, to displace the lung parenchyma inferiorly, thereby manipulating the airway.

In another embodiment of the invention, a method of manipulating the airway is provided. A patient with sleep-disordered breathing is identified, the diaphragm is at least intermittently activated to increase lung volume and the airway is displaced inferiorly. In one embodiment of the invention, the diaphragm is directly stimulated by an electrode to activate the diaphragm. In another embodiment, the diaphragm is stimulated indirectly by stimulating the phrenic nerve. In one embodiment, stimulation is performed with a partially implantable device, such as an electrode with leads exiting the skin and attaching to an external power source and controller. In another embodiment, stimulation is performed by a fully implantable device comprising an electrode lead connected to a housing with a power source and controller. The housing can be implanted subcutaneously, similar to a cardiac pacemaker.

In other embodiments, the invention further comprises a sensor for detecting native respiratory activity. Upon detection of native diaphragm activity, electrical stimulation is provided to augment the native respiratory activity. In one embodiment, the phrenic nerve is stimulated by applying electrical current to the phrenic nerve with electrodes that are positioned over the cervical vertebrae between C3 and C7. In one embodiment, the electrodes are placed both posterior and anterior between C3 and C5. In another embodiment, the diaphragm is directly stimulated by an implantable electrode.

In another embodiment, a stimulation device is provided that comprises a generally flat back plate that is configured to be placed below a patient's back when the patient is lying down. Further, at least two electrodes are coupled to the stimulation device to electrically stimulate the patient. For example, the electrodes may be employed to electrically stimulate the phrenic nerve in a manner similar to other embodiments described herein.

The electrical current may be provided in multiphasic form. For example, the wave form may be biphasic, including asymmetrical biphasic. Depending on the particular treatment, the electrical signal may be within certain current ranges, certain frequency ranges, and certain pulse width ranges. In one example, biphasic electrical current may be used that is in the range from about 100 milliamps to about 2,000 milliamps at a frequency in the range from about 10 Hz to about 100 Hz, and in pulse widths in the range from about 1 microsecond to about 5 milliseconds. The stimulator may be activated from about 10 to about 100 times per minute.

Figure 29A:
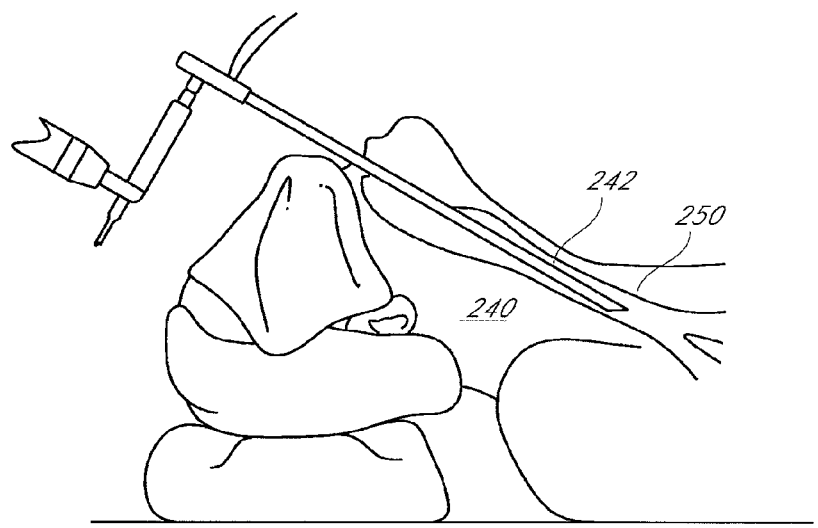
FIGS. 29A and 29B depict an embodiment of the invention for bronchoscopically accessing the trachea.
Figure 29B:
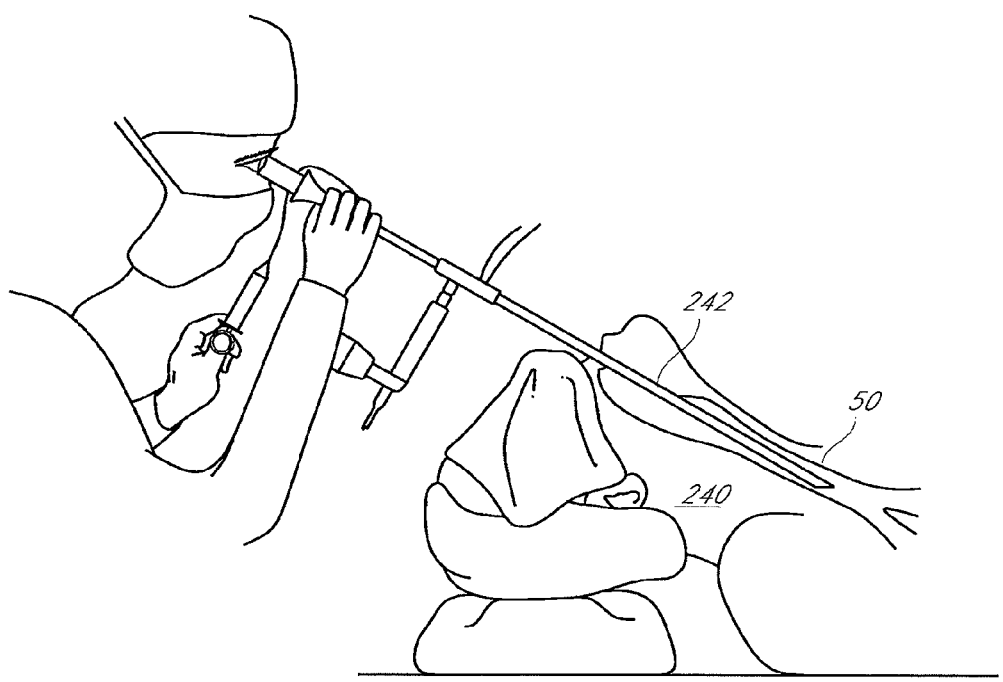

As shown in FIGS. 29A and 29B, the patient 240 may be premedicated with atropine to decrease respiratory secretions and also codeine to provide patient comfort and decrease cough during the procedure. The patient may also be provided supplemental oxygen by nasal cannula to keep hemoglobin saturation at least about 90% during the procedure. Topical lidocaine or a superior laryngeal nerve block is used to anesthetize the pharynx and vocal cords. The bronchoscope 242 may be passed through the nostril using lidocaine jelly for anesthesia and lubrication. Alternatively, the bronchoscope 242 may be passed orally after insertion of an oral airway or bite-block. After the nasopharynx and larynx are inspected, the scope is passed through the vocal cords during inspiration.

Upon access to the trachea 50, the device can be implanted as previously described for the particular embodiment of the invention. Any of a variety of bronchoscopic tools may be used to facilitate implantation of the device, including but not limited to forceps, suturing tools, scissors, staplers and others. Following tracheal manipulation, the bronchoscope 242 is withdrawn and erect PA and lateral chest x-rays are obtained to check for pneumothorax.

To provide access to the airway, one embodiment of the invention provides an open surgical approach to the trachea. The patient undergoes general inhalational anesthesia with endotracheal intubation for mechanical respiratory support. The patient is positioned and draped on the operating table in the usual sterile fashion.

As depicted in FIGS. 30A through 30C, in one embodiment of the invention, the cervical portion 250 of the trachea is accessed. The patient's neck is hyperflexed to enhance exposure to the surgical site. In some instances, hyperflexion of the neck may also displace up to about 50% of the trachea above the thoracic outlet. A horizontal incision 252 is made over the second or third tracheal ring after the level of the cricoid cartilage 14 has been identified. The platysma muscle 254 is horizontally divided and the strap muscles of the neck are separated from the midline. The cricoid cartilage is identified and the thyroid isthmus may be divided and sutured to facilitate access to the tracheal rings, if necessary. With the second through fourth tracheal rings exposed, implantation of the particular embodiment of the device may proceed.

Additional dissection along the airway may be performed as needed. Referring to FIG. 30C, if access to the lower tracheal rings is desired, the upper portion of the sternum 250 may be split to provide expanded access to the upper half of the trachea 50. Access to the tracheal lumen may be performed by piercing the membrane between the exposed tracheal rings. If access to the tracheal lumen is desired, the second and third tracheal rings may be vertically incised to enlarge access, as depicted in FIG. 30B. The fourth tracheal ring may be partially incised if necessary. Smooth thyroid pole retractors are inserted into the tracheal incision to spread the opening. In one embodiment, upon implantation of the tracheal manipulation device, the trachea is checked for adequate vertical mobility to provide swallowing ability. Closure of the surgical site is performed with simple skin sutures.

Figure 31:
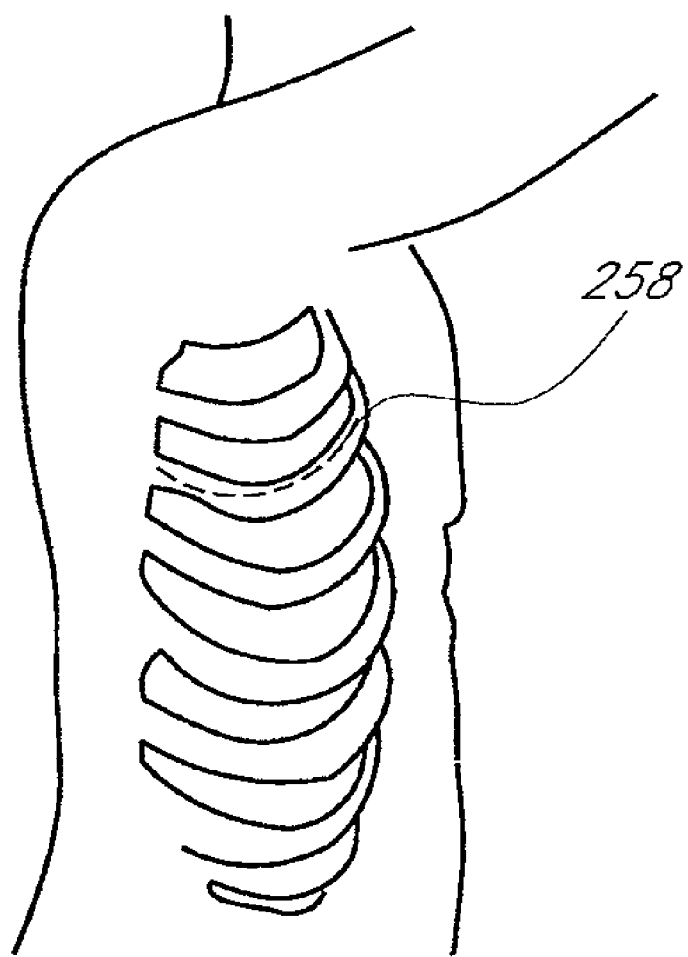
FIG. 31 shows another embodiment for surgically accessing the trachea in the thoracic cavity.

In embodiments of the invention where access to the lower trachea, carina and/or mainstem bronchi is desired, a thoracotomy approach may be used. During intubation, the left side of the lung may be selectively intubated so that the right lung may be collapsed to increase surgical access to the trachea. The patient is positioned in the left lateral decubitis position. The two ends of the surgical table may be lowered in an inverted V-shape to further separate the ribs during the surgery. As shown in FIG. 31, an incision 258 is made obliquely along the right fourth anterior intercostal space and is extended behind the scapula if posterior tracheal access is required. The incision 258 is made down to the subcutaneous fat and then extended until the pleural space is reached. A rush of air should be heard and a finger is inserted into the pleural space to check for pleural adhesions before completing the thoracotomy incision. The lower trachea is exposed for implantation of the tracheal manipulation device. After placement of the implant, a chest tube is placed through the incision to the apex of the lung and connected to a suction device. The chest tube is secured to the chest wall with sutures and the thoracotomy incision is closed. The chest tube site is covered with Xeroform gauze and a chest x-ray is obtained to confirm function of the chest tube. The patient is withdrawn from general anesthesia but remains intubated until weaned from respiratory support.

In embodiments of the invention where access to the lower trachea, carina and/or mainstem bronchi is desired through a minimally invasive procedure, video assisted thoracoscopic surgery may be performed. The patient undergoes general inhalational anesthesia with selective endotracheal intubation of the left lung. The patient is positioned in the left lateral decubitis position and draped in the usual sterile fashion. A 1.5 cm horizontal incision down to the subcutaneous fat is made along the anterolateral surface of the right sixth intercostal space. With a tonsillar clamp, a tract is created from the incision site superiorly, posteriorly and immediately above the superior edge of the 6th rib to avoid injury to the neurovascular bundle. Upon entering the pleural space, a rush of air should be heard. A finger is placed through the tract into the pleural space to confirm that no adhesions are present.

Figure 32:
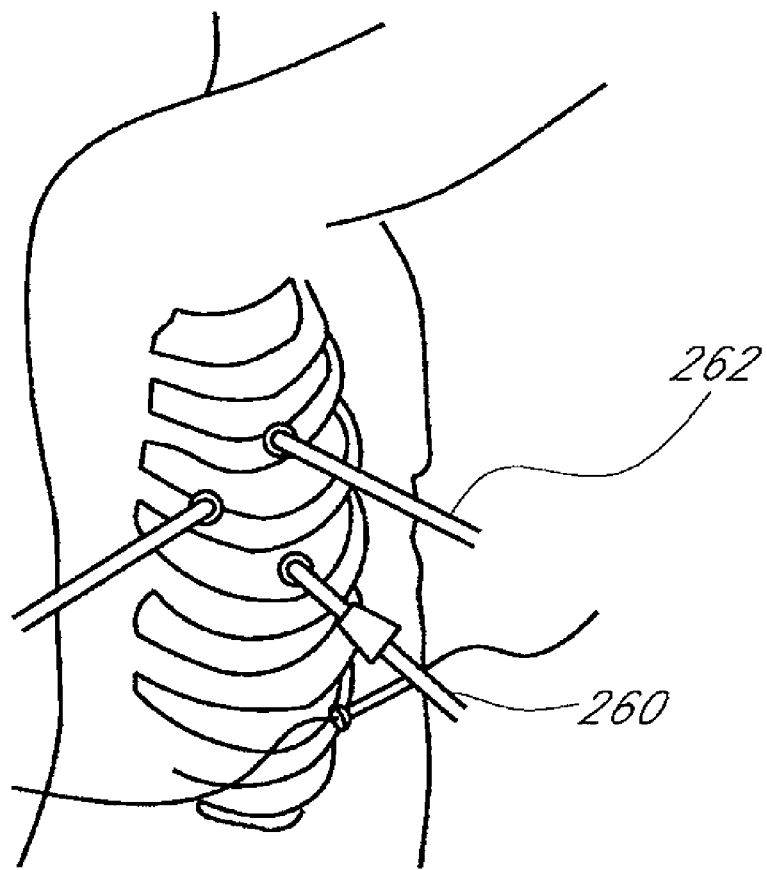
FIG. 32 shows a video-assisted thoracoscopic surgery (VATS) approach for accessing the trachea in the thoracic cavity.

As depicted in FIG. 32, the primary trocar 260 or thoracopic port providing visualization of the thoracic cavity is then inserted through the tract. Secondary ports 262, 264 are similarly inserted through smaller incisions at the 6th right posterolateral intercostal space and 4th right intercostal space to provide additional access for thoracopic tools to implant the tracheal manipulation device. Such devices include but are not limited to graspers, dissectors, scissors, needle holders, stapling devices, clip appliers, suction/irrigation systems, intracorporeal suturing devices, ultrasonic coagulators as well as instruments for delivering the particular tracheal device into the thoracic cavity and attaching the device to the thoracic structures with respect to the trachea. Such devices typically have diameters from about 3 mm to about 12 mm.

Upon completion of the procedure, the insertion sites of the secondary ports 262, 264 are sutured and covered with Xeroform gauze. The primary port 260 is removed and replaced with a chest tube inserted into the right apical space. The chest tube is connected to suction and sutured to the chest wall. The chest tube site is covered with Xeroform gauze and dressed. A chest X-ray is obtained and general anesthesia is withdrawn.

Figure 33A:
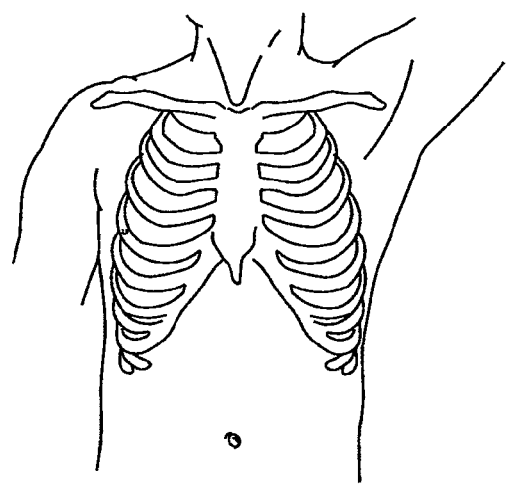
FIGS. 33A through 33C illustrate a minimally invasive approach for inserting a tracheal manipulation implant into the pleural apices of the thoracic cavity.
Figures 33B, 33C:
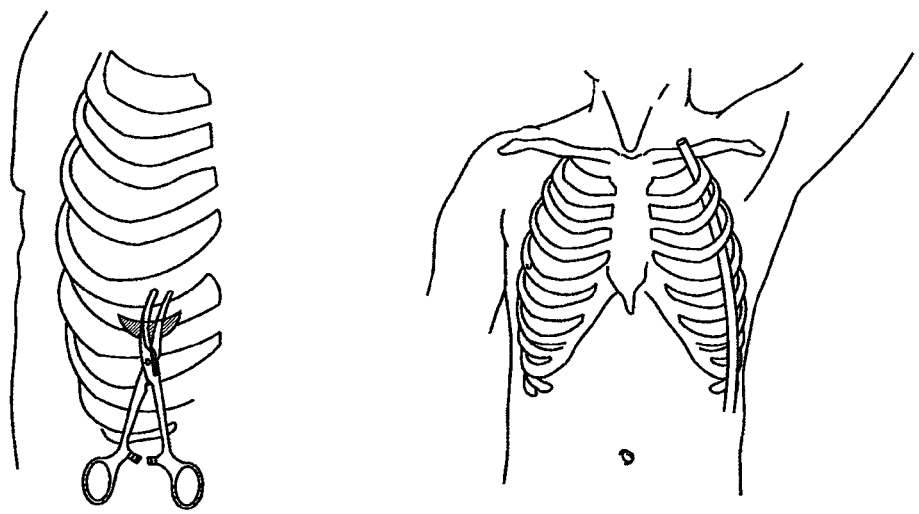

In another embodiment of the invention, FIGS. 33A to 33C illustrate a method for accessing the pleural cavity. The patient is prepped and draped in the usual sterile fashion. The patient is positioned in the right lateral decubitis position. See FIG. 33A. In FIG. 33B, an incision is made obliquely along the left fourth anterior intercostal space and is extended behind the scapula if posterior tracheal access is required. The incision is made down to the subcutaneous fat and then extended until the pleural space is reached. A rush of air should be heard and a finger is inserted into the pleural space to check of pleural adhesions. The catheter or implant delivery system is inserted into pleural space. If access to the apex of the pleural cavity is desired, as in FIG. 33C, the catheter or delivery system may be inserted by tracking the tip against the ribcage until the apex is reached, as visualized on fluoroscopy. In another embodiment, an incision closer to the apex of the pleural cavity is made to implant the device, but the risk of inadvertent damage to the subclavian blood vessels increases.

While this invention has been particularly shown and described with references to embodiments thereof, it will be understood by those skilled in the art that various changes in form and details may be made therein without departing from the scope of the invention. For all of the embodiments described above, the steps of the methods need not be performed sequentially.

What is claimed is:

1. A method of treating apnea, comprising the steps of:
    positioning a device in a body using a delivery tool;
    securing a device with respect to a trachea, the trachea having a superior direction and an inferior direction;
    manipulating the device to contract at least a portion of the trachea longitudinally in the inferior direction; and
    removing the delivery tool wherein the device is implanted in the body.

2. A method of treating apnea as in claim 1, wherein the securing step comprises securing the device to the trachea.

3. A method of treating apnea as in claim 1, additionally comprising the step of positioning the device within the trachea.

4. A method of treating apnea as in claim 1, wherein the securing step comprises securing the device to tissue adjacent the trachea.

5. A method of treating apnea as in claim 4, wherein the securing step comprises securing the device to the esophagus.

6. A method of treating apnea as in claim 1, wherein the manipulating step comprises placing the device under tension to pull the trachea inferiorly.

7. A method of treating apnea as in claim 1, wherein the manipulating step comprises radially expanding the device within the trachea.

8. A method of treating apnea as in claim 1, wherein the trachea divides into a first and second bronchial tubes having an angle therebetween, and the manipulating step comprises adjusting the device to change the angle.

9. A method of treating apnea as in claim 1, comprising securing a first portion of the device at a first attachment point, securing a second portion of the device at a second attachment point and reducing the distance between the first and second attachment points.

10. A method of treating apnea as in claim 1, wherein the manipulating step comprises expanding the device at the apex of the pleural cavity.

11. A method of treating apnea, comprising the steps of positioning a device in a body using a delivery tool;
    securing the device with respect to a trachea, the trachea having a superior direction and an inferior direction;
    manipulating the device to longitudinally shorten the trachea and resist movement of at least a portion of the trachea in the superior direction; and
    removing the delivery tool wherein the device is implanted in the body.

12. A method of treating apnea, comprising the steps of:
    positioning a device into a body using a delivery tool;
    securing the device with respect to a trachea, the trachea having a first wall tension and a second wall tension;
    manipulating the device to longitudinally shorten the trachea and alter at least a portion of the trachea from the first wall tension to the second wall tension; and
    removing the delivery tool wherein the device is implanted in the body.

13. A method of treating a patient, comprising the steps of
    providing a tracheal device having a first end with a first attachment structure, and a second end with a second attachment structure;
    attaching the first attachment structure to a first attachment point on the trachea;
    attaching the second attachment structure to a second attachment point on the trachea; and
    shortening the trachea longitudinally between the first and second attachment points.

14. A tracheal implant, comprising:
    an elongate body, adapted for positioning with respect to the trachea of a patient;
    a first attachment structure on the body; and
    a second attachment structure on the body, spaced apart from the first attachment structure;
    wherein the implant is configured for positioning with respect to the trachea and attaching to a trachea wall at a first attachment point on the tracheal wall and a second attachment point on the tracheal wall to reduce the effective length of the trachea longitudinally between the first and second attachment points.

15. The tracheal implant of claim 14, wherein the implant comprises at least one helical spring.

16. The tracheal implant of claim 14, wherein the elongate body of the implant is configured for placement on the external surface of the trachea.

* * * * *